United States Patent
Tanaka et al.

(10) Patent No.: US 10,125,074 B2
(45) Date of Patent: Nov. 13, 2018

(54) 5-SUBSTITUTED-5-HYDROXY-5-ARYL-3-OXO-PENTANOATE DERIVATIVES AND THEIR ENANTIOPURE FORMS

(71) Applicant: OKINAWA INSTITUTE OF SCIENCE AND TECHNOLOGY SCHOOL CORPORATION, Okinawa (JP)

(72) Inventors: Fujie Tanaka, Okinawa (JP); Dongxin Zhang, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 15/560,868

(22) PCT Filed: Feb. 1, 2016

(86) PCT No.: PCT/JP2016/000507
§ 371 (c)(1),
(2) Date: Sep. 22, 2017

(87) PCT Pub. No.: WO2016/151990
PCT Pub. Date: Sep. 29, 2016

(65) Prior Publication Data
US 2018/0118648 A1    May 3, 2018

Related U.S. Application Data

(60) Provisional application No. 62/137,387, filed on Mar. 24, 2015.

(30) Foreign Application Priority Data

Jul. 31, 2015  (JP) ................. 2015-152438

(51) Int. Cl.
| | |
|---|---|
| C07C 49/00 | (2006.01) |
| C07C 69/00 | (2006.01) |
| C07C 227/30 | (2006.01) |
| C07C 49/753 | (2006.01) |
| C07C 69/738 | (2006.01) |
| C07D 333/22 | (2006.01) |
| C07D 333/24 | (2006.01) |
| C07C 227/10 | (2006.01) |
| C07C 229/34 | (2006.01) |
| C07C 49/255 | (2006.01) |
| C07C 49/747 | (2006.01) |
| C07C 227/34 | (2006.01) |
| C07C 227/42 | (2006.01) |
| A61K 31/02 | (2006.01) |
| A61K 31/045 | (2006.01) |

(52) U.S. Cl.
CPC .......... *C07C 49/753* (2013.01); *C07C 49/255* (2013.01); *C07C 49/747* (2013.01); *C07C 69/738* (2013.01); *C07C 227/10* (2013.01); *C07C 227/30* (2013.01); *C07C 227/34* (2013.01); *C07C 227/42* (2013.01); *C07C 229/34* (2013.01); *C07D 333/22* (2013.01); *C07D 333/24* (2013.01); *A61K 31/02* (2013.01); *A61K 31/045* (2013.01); *C07C 2601/10* (2017.05); *C07C 2601/16* (2017.05)

(58) Field of Classification Search
CPC ... C07C 49/753; C07C 49/255; C07C 49/747; C07C 69/738; C07C 227/10; C07C 227/30
See application file for complete search history.

(56) References Cited

FOREIGN PATENT DOCUMENTS

| CN | 103172539 | 6/2013 |
|---|---|---|
| WO | 2013/021949 | 2/2013 |

OTHER PUBLICATIONS

International Search Report dated Mar. 29, 2016 in International (PCT) Application No. PCT/JP2016/000507.
Luo S. et al., "Asymmetric Direct Aldol Reactions of Pyruvic Derivatives", Organic Letters, vol. 10, No. 9, 2008, pp. 1775-1778.
Markert M. et al., "Amine-Catalyzed Direct Aldol Addition", J. Am. Chem. Soc., vol. 129, 2007, pp. 7258-7259.
Zhang D. et al., "Aldol reactions using aryl trifluoromethyl ketones as electrophiles catalyzed by 1,8-diazabicyclo [5.4.0]undec-7-ene (DBU) under solvent free mild conditions", the 135th Annual Meeting of the Pharmaceutical Society of Japan in Kobe (Web page), Feb. 2, 2015, http://nenkai.pharm.or.jp/135/pc/ipdfview.asp?i=146.
Zhang D. et al., "Aldol reactions using aryl trifluoromethyl ketones as electrophiles catalyzed by 1,8-diazabicyclo[5.4.0]undec-7-ene (DBU) under solvent free mild conditions", Abstracts of the 135th Annual Meeting of the Pharmaceutical Society of Japan in Kobe, Mar. 5, 2015, p. 206.
Zhang D. et al., "Aldol reactions using trifluoromethyl ketones as electrophiles catalyzed by 1,8-diazabicyclo [5.4.0]undec-7-ene (DBU) under solvent-free mild conditions", The 135th Annual Meeting of the Pharmaceutical Society of Japan in Kobe (Poster Presentation), Mar. 27, 2015.
Zhang D. et al., "Aldol Reactions of Ketone Donors with Aryl Trifluoromethyl Ketone Acceptors Catalyzed by 1,8-Diazabicyclo [5.4.0]undec-7-ene (DBU) for Concise Access to Aryl- and Trifluoromethyl Substituted Tertiary Alcohols", Advanced Synthesis & Catalysis, vol. 357, Oct. 13, 2015, pp. 3458-3462.

(Continued)

*Primary Examiner* — Sikarl A Witherspoon
(74) *Attorney, Agent, or Firm* — Wenderoth, Lind & Ponack, L.L.P.

(57) ABSTRACT

The present invention relates to novel tertiary alcohol derivatives substituted with aryl and trifluoromethyl, and optical isomers thereof. In addition, the present invention also relates to methods for the preparation and use as enantiomer recognition agent thereof. The present invention provides pharmaceutical composition and use as therapeutically active substance thereof.

11 Claims, No Drawings

(56) References Cited

OTHER PUBLICATIONS

Tao et al., "Solvent free synthesis of trifluoromethyl tertiary alcohols by cross Aldol reaction", Chinese Chemical Letters, vol. 26, Apr. 21, 2015, pp. 1046-1049.
Blumel et al., "Asymmetric Organocatalytic Synthesis of Highly Functionalized Spirocyclohexane Indandiones via a One-Pot Michael/Michael/Aldol Sequence", Synthesis, vol. 47, Aug. 14, 2015, pp. 3618-3628.
Muller et al., "Fluorine in Pharmaceuticals: Looking Beyond Intuition", Science, vol. 317, Sep. 28, 2007, pp. 1881-1886.
Written Opinion dated Mar. 29, 2016 in International (PCT) Application No. PCT/JP2016/000507.

5-SUBSTITUTED-5-HYDROXY-5-ARYL-3-OXO-PENTANOATE DERIVATIVES AND THEIR ENANTIOPURE FORMS

TECHNICAL FIELD

The present invention relates to novel tertiary alcohol derivatives substituted with aryl and trifluoromethyl, and optical isomers thereof. In addition, the present invention also relates to methods for the preparation of the tertiary alcohols and their use as enantiomer recognition agent thereof. The present invention also provides pharmaceutical composition comprising the tertiary alcohols and their use as therapeutically active substance thereof.

BACKGROUND ART

Tertiary alcohol compounds substituted with aryl and trifluoromethyl are important as bioactive substance, enantiomer recognition agent, and synthetic syntons and building blocks (NPL1). Further, compounds with aryl and trifluoromethyl such as Mosher's acid, or α-methoxy-α-trifluoromethylphenylacetic acid (MTPA) are used as a chiral derivatizing agent.

Aldol reaction of aryl and trifluoromethyl substituted ketone has been reported. However, use of 1,8-diazabicyclo[5.4.0]undec-7-ene (DBU) as catalyst has not been reported for the reaction. Further, the method of preparation for 5-trifluoromethyl-5-hydroxy-5-aryl-3-oxo-petanoate derivatives as enantiomer has not been reported.

CITATION LIST

Non Patent Literature

NPL 1: K. Mueller, C. Faeh and F. Diederich, Science 2007, 317, 1881-1886.

SUMMARY OF INVENTION

Technical Problem

The technical problem to be solved by the present invention is that of providing novel tertiary alcohol derivatives substituted with aryl and trifluoromethyl, and optical isomers thereof which may be used as bioactive substance, enantiomer recognition agent, and synthetic syntons and building blocks. The technical problem to be solved by the present invention is also that of providing the methods for preparation of the tertiary alcohols and their use as enantiomer recognition agent. In addition, the present invention also addresses the technical problem of providing pharmaceutical composition comprising the tertiary alcohols and their use as therapeutically active substance.

Solution to Problem

The present invention can provide novel tertiary alcohol derivatives substituted with aryl and trifluoromethyl by aldol reaction by use of ketone donor, tertiary alcohol substituted with aryl-trifluoromehtyl, and 1,8-diazabicyclo[5.4.0]undec-7-ene (DBU) as catalyst.

The present invention relates as follows.
(1) Compound of formula I

[Chem. 1]

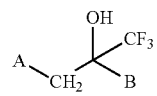

wherein
A is

[Chem. 2]

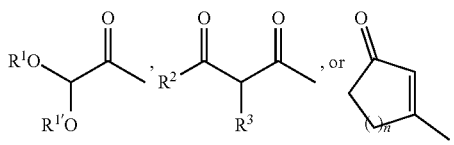

B is aryl which is substituted with by one or more groups selected from the group consisting of $C_{1-7}$-alkyl, halogen, halogen-$C_{1-7}$-alkyl, $C_{1-7}$-alkoxy, halogen-$C_{1-7}$-alkoxy, hydroxy, cyano, and nitro, or is heteroaryl, which is unsubstitued or substituted with by one or more groups selected from the group consisting of $C_{1-7}$-alkyl, halogen, halogen-$C_{1-7}$-alkyl, $C_{1-7}$-alkoxy, halogen-$C_{1-7}$-alkoxy, hydroxy, cyano, and nitro;

$R^1$ and $R^{1'}$ may be same or different and each is independently selected from the group consisting of $C_{1-7}$-alkyl, halogen-$C_{1-7}$-alkyl, and $C_{1-7}$-alkyl substituted with one or more $C_{1-7}$-alkoxy; or $R^1$ and $R^{1'}$ may together form $C_{1-7}$alkylene;

$R^2$ is selected from the group consisting of $C_{1-7}$-alkoxy, $C_{3-7}$-cycloalkyloxy, halogen-$C_{1-7}$-alkoxy, $C_{1-7}$-alkoxy substituted with one or more $C_{1-7}$-alkyl, and hydroxy;

$R^3$ is selected from the group consisting of hydrogen, $C_{1-7}$-alkyl, halogen-$C_{1-7}$-alkyl, hydroxy-$C_{1-7}$-alkyl, $C_{1-7}$-alkoxy, and halogen-$C_{1-7}$-alkoxy;

n is 1, 2, 3, or 4;
or salt thereof.

(2) Compound of formula I or salt thereof according to (1), wherein

B is aryl which is substituted with by one or more groups selected from the group consisting of $C_{1-7}$-alkyl, halogen, halogen-$C_{1-7}$-alkyl, $C_{1-7}$-alkoxy, and halogen-$C_{1-7}$-alkoxy, or is heteroaryl which is unsubstitued or substituted with by one or more groups selected from the group consisting of $C_{1-7}$-alkyl, halogen, halogen-$C_{1-7}$-alkyl, $C_{1-7}$-alkoxy, and halogen-$C_{1-7}$-alkoxy.

(3) Compound of formula I or salt thereof according to (1) or (2) wherein $R^1$ and $R^{1'}$ may be same or different and each is independently selected from the group consisting of $C_{1-7}$-alkyl, halogen-$C_{1-7}$-alkyl and $C_{1-7}$-alkyl substituted with one or more $C_{1-7}$-alkoxy.

(4) Compound of formula I or salt thereof according to any one of (1) to (3), wherein $R^2$ is selected from the group consisting of $C_{1-7}$-alkyl, halogen-$C_{1-7}$-alkyl, $C_{1-7}$-alkoxy, halogen-$C_{1-7}$-alkoxy, $C_{1-7}$-alkoxy substituted with one or more $C_{1-7}$-alkyl (5) Compound of formula I or salt thereof according to any one of (1) to (4), wherein $R^3$ is selected from the group consisting of hydrogen, halogen and $C_{1-7}$-alkyl.

(6) Compound of formula I or salt thereof according to any one of (1) to (5), wherein n is 1 or 2.

(7) Compounds of formula I according to any one of (1) to (6), selected from the group consisting of 5,5,5-trifluoro-4-hydroxy-1,1-dimethoxy-4-phenylpentan-2-one,
(R)-5,5,5-trifluoro-4-hydroxy-1,1-dimethoxy-4-phenylpentan-2-one,
(S)-5,5,5-trifluoro-4-hydroxy-1,1-dimethoxy-4-phenylpentan-2-one,
4-(4-chlorophenyl)-5,5,5-trifluoro-4-hydroxy-1,1-dimethoxypentan-2-one,
(R)-4-(4-chlorophenyl)-5,5,5-trifluoro-4-hydroxy-1,1-dimethoxypentan-2-one,
(S)-4-(4-chlorophenyl)-5,5,5-trifluoro-4-hydroxy-1,1-dimethoxypentan-2-one,
4-(4-bromophenyl)-5,5,5-trifluoro-4-hydroxy-1,1-dimethoxypentan-2-one,
(R)-4-(4-bromophenyl)-5,5,5-trifluoro-4-hydroxy-1,1-dimethoxypentan-2-one,
(S)-4-(4-bromophenyl)-5,5,5-trifluoro-4-hydroxy-1,1-dimethoxypentan-2-one,
5,5,5-trifluoro-4-hydroxy-1,1-dimethoxy-4-(4-(trifluoromethyl)phenyl)pentan-2-one,
(R)-5,5,5-trifluoro-4-hydroxy-1,1-dimethoxy-4-(4-(trifluoromethyl)phenyl)pentan-2-one,
(S)-5,5,5-trifluoro-4-hydroxy-1,1-dimethoxy-4-(4-(trifluoromethyl)phenyl)pentan-2-one,
5,5,5-trifluoro-4-hydroxy-1,1-dimethoxy-4-(p-tolyl)pentan-2-one,
(R)-5,5,5-trifluoro-4-hydroxy-1,1-dimethoxy-4-(p-tolyl)pentan-2-one,
(S)-5,5,5-trifluoro-4-hydroxy-1,1-dimethoxy-4-(p-tolyl)pentan-2-one,
5,5,5-trifluoro-4-hydroxy-1,1-dimethoxy-4-(4-methoxyphenyl)pentan-2-one,
(R)-5,5,5-trifluoro-4-hydroxy-1,1-dimethoxy-4-(4-methoxyphenyl)pentan-2-one,
(S)-5,5,5-trifluoro-4-hydroxy-1,1-dimethoxy-4-(4-methoxyphenyl)pentan-2-one,
5,5,5-trifluoro-4-hydroxy-1,1-dimethoxy-4-(thiophen-2-yl)pentan-2-one,
(R)-5,5,5-trifluoro-4-hydroxy-1,1-dimethoxy-4-(thiophen-2-yl)pentan-2-one,
(S)-5,5,5-trifluoro-4-hydroxy-1,1-dimethoxy-4-(thiophen-2-yl)pentan-2-one,
5,5,5-trifluoro-4-hydroxy-1,1-dimethoxy-4-(1H-pyrrol-2-yl)pentan-2-one,
(R)-5,5,5-trifluoro-4-hydroxy-1,1-dimethoxy-4-(1H-pyrrol-2-yl)pentan-2-one,
(S)-5,5,5-trifluoro-4-hydroxy-1,1-dimethoxy-4-(1H-pyrrol-2-yl)pentan-2-one,
ethyl 6,6,6-trifluoro-5-hydroxy-3-oxo-5-phenylhexanoate,
(R)-ethyl 6,6,6-trifluoro-5-hydroxy-3-oxo-5-phenylhexanoate,
(S)-ethyl 6,6,6-trifluoro-5-hydroxy-3-oxo-5-phenylhexanoate,
ethyl 6,6,6-trifluoro-5-hydroxy-2-methyl-3-oxo-5-phenylhexanoate,
(R)-ethyl 6,6,6-trifluoro-5-hydroxy-2-methyl-3-oxo-5-phenylhexanoate,
(S)-ethyl 6,6,6-trifluoro-5-hydroxy-2-methyl-3-oxo-5-phenylhexanoate,
ethyl 6,6,6-trifluoro-5-hydroxy-5-(4-methoxyphenyl)-3-oxohexanoate,
(R)-ethyl 6,6,6-trifluoro-5-hydroxy-5-(4-methoxyphenyl)-3-oxohexanoate,
(S)-ethyl 6,6,6-trifluoro-5-hydroxy-5-(4-methoxyphenyl)-3-oxohexanoate,
ethyl 5-(4-chlorophenyl)-6,6,6-trifluoro-5-hydroxy-3-oxohexanoate,
(R)-ethyl 5-(4-chlorophenyl)-6,6,6-trifluoro-5-hydroxy-3-oxohexanoate,
(S)-ethyl 5-(4-chlorophenyl)-6,6,6-trifluoro-5-hydroxy-3-oxohexanoate,
ethyl 6,6,6-trifluoro-5-hydroxy-3-oxo-5-(thiophen-2-yl)hexanoate,
(R)-ethyl 6,6,6-trifluoro-5-hydroxy-3-oxo-5-(thiophen-2-yl)hexanoate,
(S)-ethyl 6,6,6-trifluoro-5-hydroxy-3-oxo-5-(thiophen-2-yl)hexanoate,
ethyl 6,6,6-trifluoro-5-hydroxy-5-(4-methoxyphenyl)-2-methyl-3-oxohexanoate,
(R)-ethyl 6,6,6-trifluoro-5-hydroxy-5-(4-methoxyphenyl)-2-methyl-3-oxohexanoate,
(S)-ethyl 6,6,6-trifluoro-5-hydroxy-5-(4-methoxyphenyl)-2-methyl-3-oxohexanoate,
ethyl 5-(4-chlorophenyl)-6,6,6-trifluoro-5-hydroxy-2-methyl-3-oxohexanoate,
(R)-ethyl 5-(4-chlorophenyl)-6,6,6-trifluoro-5-hydroxy-2-methyl-3-oxohexanoate,
(S)-ethyl 5-(4-chlorophenyl)-6,6,6-trifluoro-5-hydroxy-2-methyl-3-oxohexanoate,
ethyl 6,6,6-trifluoro-5-hydroxy-2-methyl-3-oxo-5-(thiophen-2-yl)hexanoate,
(R)-ethyl 6,6,6-trifluoro-5-hydroxy-2-methyl-3-oxo-5-(thiophen-2-yl)hexanoate,
(S)-ethyl 6,6,6-trifluoro-5-hydroxy-2-methyl-3-oxo-5-(thiophen-2-yl)hexanoate,
(R)-ethyl 6,6,6-trifluoro-5-hydroxy-5-phenyl-3-(((R)-1-phenylethyl)amino)hex-2-enoate,
(S)-ethyl 6,6,6-trifluoro-5-hydroxy-3-(((R)-1-phenylethyl)amino)-5-(thiophen-2-yl)hex-2-enoate,
3-(3,3,3-trifluoro-2-hydroxy-2-phenylpropyl)cyclohex-2-enone,
(R)-3-(3,3,3-trifluoro-2-hydroxy-2-phenyl propyl)cyclohex-2-enone,
(S)-3-(3,3,3-trifluoro-2-hydroxy-2-phenyl propyl)cyclohex-2-enone,
3-(3,3,3-trifluoro-2-hydroxy-2-(p-tolyl)propyl)cyclohex-2-enone,
(R)-3-(3,3,3-trifluoro-2-hydroxy-2-(p-tolyl)propyl)cyclohex-2-enone,
(S)-3-(3,3,3-trifluoro-2-hydroxy-2-(p-tolyl)propyl)cyclohex-2-enone,
3-(3,3,3-trifluoro-2-hydroxy-2-(4-methoxyphenyl)propyl)cyclohex-2-enone,
(R)-3-(3,3,3-trifluoro-2-hydroxy-2-(4-methoxyphenyl)propyl)cyclohex-2-enone,
(S)-3-(3,3,3-trifluoro-2-hydroxy-2-(4-methoxyphenyl)propyl)cyclohex-2-enone,
3-(2-(4-chlorophenyl)-3,3,3-trifluoro-2-hydroxypropyl)cyclohex-2-enone,
(R)-3-(2-(4-chlorophenyl)-3,3,3-trifluoro-2-hydroxypropyl)cyclohex-2-enone,
(S)-3-(2-(4-chlorophenyl)-3,3,3-trifluoro-2-hydroxypropyl)cyclohex-2-enone,
3-(2-(4-bromophenyl)-3,3,3-trifluoro-2-hydroxypropyl)cyclohex-2-enone, (R)-3-(2-(4-bromophenyl)-3,3,3-trifluoro-2-hydroxypropyl) cyclohex-2-enone,
(S)-3-(2-(4-bromophenyl)-3,3,3-trifluoro-2-hydroxypropyl) cyclohex-2-enone,
3-(3,3,3-trifluoro-2-hydroxy-2-(4-(trifluoromethyl)phenyl) propyl)cyclohex-2-enone,
(R)-3-(3,3,3-trifluoro-2-hydroxy-2-(4-(trifluoromethyl)phenyl)propyl)cyclohex-2-enone,
(S)-3-(3,3,3-trifluoro-2-hydroxy-2-(4-(trifluoromethyl)phenyl)propyl)cyclohex-2-enone,
3-(3,3,3-trifluoro-2-hydroxy-2-(thiophen-2-yl)propyl)cyclohex-2-enone,
(R)-3-(3,3,3-trifluoro-2-hydroxy-2-(thiophen-2-yl)propyl) cyclohex-2-enone,
(S)-3-(3,3,3-trifluoro-2-hydroxy-2-(thiophen-2-yl)propyl) cyclohex-2-enone,
3-(3,3,3-trifluoro-2-hydroxy-2-phenylpropyl)cyclopent-2-enone,
(R)-3-(3,3,3-trifluoro-2-hydroxy-2-phenylpropyl)cyclopent-2-enone,
(S)-3-(3,3,3-trifluoro-2-hydroxy-2-phenylpropyl)cyclopent-2-enone,
3-(3,3,3-trifluoro-2-hydroxy-2-(4-methoxyphenyl)propyl) cyclopent-2-enone,
(R)-3-(3,3,3-trifluoro-2-hydroxy-2-(4-methoxyphenyl)propyl)cyclopent-2-enone,
3,3,3-trifluoro-2-hydroxy-2-(4-methoxyphenyl)propyl)cyclopent-2-enone,
(S)-3-(3,3,3-trifluoro-2-hydroxy-2-(4-methoxyphenyl)propyl)cyclopent-2-enone,
3-(3,3,3-trifluoro-2-hydroxy-2-(4-(trifluoromethyl)phenyl) propyl)cyclopent-2-enone,
(R)-3-(3,3,3-trifluoro-2-hydroxy-2-(4-(trifluoromethyl)phenyl)propyl)cyclopent-2-enone, and
(S)-3-(3,3,3-trifluoro-2-hydroxy-2-(4-(trifluoromethyl)phenyl)propyl)cyclopent-2-enone
or salts thereof.

(8) A process for the manufacture of compound of formula I as defined in (1), which process comprises:
a) reacting compound of formula II:

[Chem. 3]

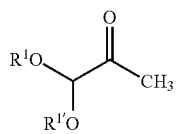

II wherein $R^1$ and $R^{1'}$ are defined in (1), with compound of formula III:

[Chem. 4]

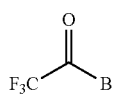

III wherein B is as defined in (1), in the presence of DBU to obtain compound of formula I-1:

[Chem. 5]

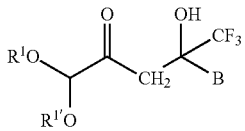

I-1 wherein $R^1$, $R^{1'}$, and B are as defined in (1), or
b) reacting compound of formula IV:

[Chem. 6]

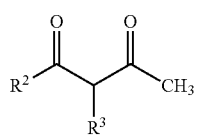

IV wherein $R^2$ and $R^3$ are as defined in (1), with compound of formula III:

[Chem. 7]

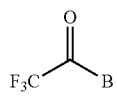

III wherein B is as defined in (1), in the presence of DBU to obtain compound of formula I-2:

[Chem. 8]

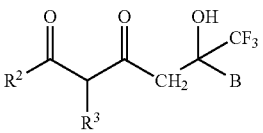

I-2 wherein $R^2$, $R^3$, and B are as defined in (1), or
c) reacting compound of formula V:

[Chem. 9]

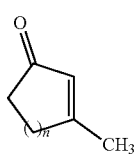

V wherein n is as defined in (1), with compound of formula III:

[Chem. 10]

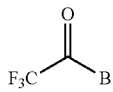
III wherein B is as defined in (1), in the presence of DBU to obtain compound of formula I-3:

[Chem. 11]

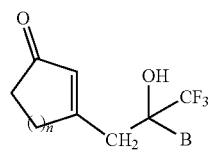
I-3 wherein B and n are as defined in (1).

(9) A process for the manufacture of compound of formula I-2a:

[Chem. 12]

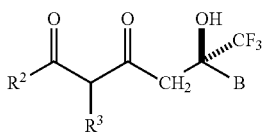
I-2a wherein $R^2$, $R^3$, and B are as define in (1), or
compound of formula I-2b:

[Chem.13]

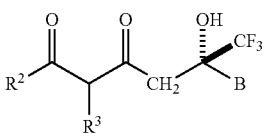
I-2b wherein $R^2$, $R^3$, and B are as define in (1), which process comprises d) reacting compound of formula I-2:

[Chem.14]

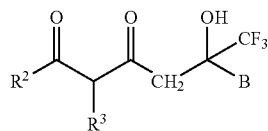
I-2 wherein $R^2$, $R^3$, and B are as define in (1), with a chiral amine:

[Chem.15]

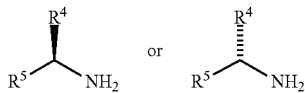

wherein $R^4$ and $R^5$ are independently each other selected from the group of $C_{1-7}$alkyl and phenyl optionally substituted with halogen, to obtain compound of formula I-2'-1:

[Chem.16]

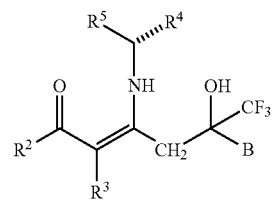
I-2'-1 wherein $R^2$, $R^3$, $R^4$, $R^5$, and B are as defined above, or compound of formula I-2'-2:

[Chem.17]

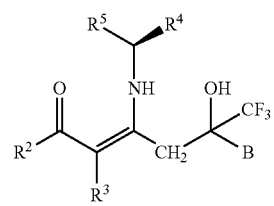
I-2'-2 wherein $R^2$, $R^3$, $R^4$, $R^5$, and B are as defined above.

(10) The process according to claim 9, which further comprises e) chiral resolution of compound of formula I-2'-1:

[Chem.18]

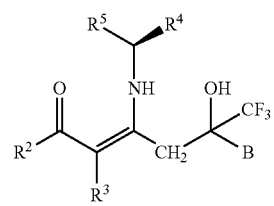
I-2'-1 wherein $R^2$, $R^3$, $R^4$, $R^5$, and B are as defined above, to obtain compound of formula I-2'-1-1:

[Chem.19]

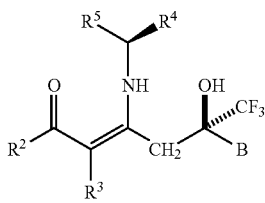

I-2'-1-1 wherein $R^2$, $R^3$, $R^4$, $R^5$, and B are as defined above, or compound of formula I-2'-1-2:

[Chem.20]

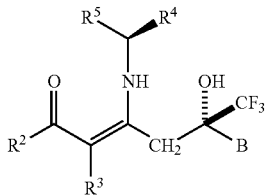

I-2'-1-2 wherein $R^2$, $R^3$, $R^4$, $R^5$, and B are as defined above.

(11) The process according to claim 10, which further comprises f) hydrolysis of compound of formula I-2'-1-1:

[Chem.21]

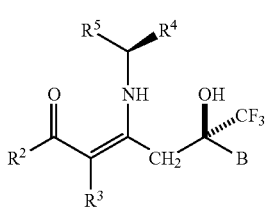

I-2'-1-1 wherein $R^2$, $R^3$, $R^4$, $R^5$, and B are as defined above, or compound of formula I-2'-1-2:

[Chem.22]

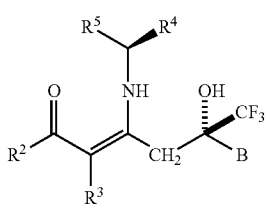

I-2'-1-2 wherein $R^2$, $R^3$, $R^4$, $R^5$, and B are as defined above, to obtain compound of formula I-2a:

[Chem.23]

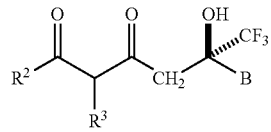

I-2a wherein $R^2$, $R^3$, and B are as defined above, or compound of formula I-2b:

[Chem.24]

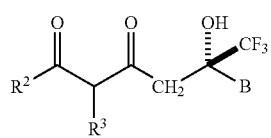

I-2b wherein $R^2$, $R^3$, and B are as defined above.

Further, the present invention relates below.

(12) Pharmaceutical composition comprising compound of formula I according to any one of (1) to (7) or pharmaceutically acceptable salt thereof.

Advantageous Effects of Invention

The present invention can provide novel tertiary alcohol derivatives substituted with aryl and trifluoromethyl, and optical isomers thereof which may be used as bioactive substance, enantiomer recognition agent, and synthetic syntons and building blocks. The present invention can also provide the methods for preparation of the tertiary alcohols and their use as enantiomer recognition agent. In addition, the present invention can also provide pharmaceutical composition comprising the tertiary alcohols and their use as therapeutically active substance.

DESCRIPTION OF EMBODIMENTS

In the present disclosure, certain details are set forth such as specific quantities, concentrations, sizes, etc. so as to provide a thorough understanding of the various embodiments disclosed herein. However, it will be apparent to those skilled in the art that the present disclosure may be practiced without such specific details. In many cases, details concerning such considerations and the like have been omitted inasmuch as such details are not necessary to obtain a complete understanding of the present disclosure and are within the skill of persons of ordinary skill in the relevant art.

The term "$C_{1-7}$alkyl", alone or in combination with other groups, denotes a monovalent linear or branched saturated hydrocarbon group of 1 to 7 carbon atoms, preferably 1 to 5 carbon atoms. Examples of $C_{1-7}$alkyl include methyl, ethyl, n-propyl, isopropyl, n-butyl, iso-butyl, sec-butyl, tert-butyl, pentyl, hexyl, and heptyl, preferably methyl, ethyl, propyl, isopropyl, n-butyl, iso-butyl, sec-butyl, tert-butyl, n-pentyl, and isopentyl, more preferably methyl, ethyl, propyl, isopropyl, isobutyl, tert-butyl, and isopentyl.

The term "$C_{1-7}$alkylene", alone or in combination with other groups, denotes a divalent linear or branched saturated hydrocarbon group of 1 to 7 carbon atoms, preferably 1 to 5 carbon atoms. Examples of $C_{1-7}$alkylene include methylene, ethylene, and propylene.

The term "$C_{3-7}$cycloalkyl", alone or in combination with other groups, denotes a monovalent saturated hydrocarbon group of 3 to 7 ring carbon atoms, preferably 3 to 6 ring carbon atoms. Examples of $C_{3-7}$cycloalkyl include cyclopropyl, cyclobutyl, cyclopentyl, and cyclohexyl.

The term "$C_{1-7}$alkoxy", alone or in combination with other groups, denotes a group of the formula $C_{1-7}$alkyl-O— wherein the term "$C_{1-7}$alkyl" is as defined above. Examples of $C_{1-7}$alkoxy include methoxy, ethoxy, n-propoxy, isopropoxy, n-butoxy, isobutoxy, secbutoxy, and tert-butoxy.

The term "$C_{3-7}$cycloalkyloxy", alone or in combination with other groups, denotes a group of the formula $C_{3-7}$alkyl-O— wherein the term "$C_{3-7}$cycloalkyl" is as defined above. Examples of $C_{3-7}$cycloalkyloxy include cyclopropyloxy, cyclobutyloxy, cyclopentyloxy, cyclohexyloxy, and cycloheptyloxy.

The term "halogen", alone or in combination with other groups, denotes halogen, for examples fluoro, chloro, bromo, or iodo, preferably fluoro, chloro, or bromo, more preferably fluoro and chloro. The term "halogen" in combination with other groups, denotes a substituent substituted with at least one halogen, preferably, 1 to 5 halogens, more preferably 1 to 4 halogens.

The term "halogen-$C_{1-7}$alkyl", alone or in combination with other groups, denotes an $C_{1-7}$alkyl group wherein at least one of the hydrogen atoms of the $C_{1-7}$alkyl group has been replaced by same or different halogen atoms, preferably 1 to 5 halogen atoms, more preferably 1 to 3 halogen atoms. Examples of haloalkyl include fluoromethyl, difluoromethyl, trifluoromethyl, 1,1,1-trifluoroethyl, 1,1,1-trifluoropropyl, and pentafluoroethyl.

The term "halogen-$C_{1-7}$alkoxy", alone or in combination with other groups, denotes an $C_{1-7}$alkoxy group wherein at least one of the hydrogen atoms of the $C_{1-7}$alkoxy group has been replaced by same or different halogen atoms, preferably 1 to 5 halogen atoms, more preferably 1 to 3 halogen atoms. Examples of haloalkoxy include fluoromethoxy, difluoromethoxy, trifluoromethoxy, 1,1,1-trifluoroethoxy, 1,1,1-trifluoropropoxy, and pentafluoroethoxy.

The term "hydroxyl" or "hydroxy", alone or in combination with other groups, refers to —OH.

The term "hydroxy-$C_{1-7}$alkyl", alone or in combination with other groups, denotes an alkyl group wherein at least one of the hydrogen atoms of the $C_{1-7}$alkyl group has been replaced by hydroxyl or hydroxy.

The term "cyano", alone or in combination with other groups, refers to —CN.

The term "nitro", alone or in combination with other groups, refers to —$NO_2$.

The term "aryl", alone or in combination with other groups, refers to a monovalent aromatic carbocyclic group comprising 6 to 14, preferably 6 to 10, carbon atoms and having at least one aromatic ring or multiple condensed rings in which at least one ring is aromatic. "aryl" is preferably $C_{6-10}$aryl. Examples of "aryl" include phenyl, 1-naphtyl and 2-naphthyl.

The term "heteroaryl", alone or in combination with other groups, refers to an aromatic carbocyclic group of having a 5 to 6 membered monocyclic ring or 9 to 10 membered bicyclic ring atoms and containing 1, 2 or 3 heteroatoms individually selected from N, O and S. Examples of "heteroaryl" include furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzimidazolyl, indolyl, indazolyl, benzothiazolyl, benzisothiazolyl, benzooxazolyl, benzoisoxazolyl, quinolinyl and isoquinolinyl, preferably furyl and thiazolyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like.

The compounds of formula I can contain several asymmetric centers and can be present in the form of optically pure enantiomers, mixtures of enantiomers, for example, racemates, optically pure diastereoisomers, mixtures of diastereoisomers, diastereoisomeric racemates or mixtures of diastereoisomeric racemates. Optically pure form can be obtained by e.g. optical resolution of racemates, asymmetric synthesis, or asymmetric chromatography (chromatography by use of chiral carrier or elutant).

According to the Cahn-Ingold-Prelog Convention the asymmetric carbon atom of the compound of formula I can be of the "R" or "S" configuration.

Abbreviation

DBU: 1,8-diazabicyclo [5.4.0]undec-7-ene

Another aspects of the invention further include the methods for the preparation of compound of formula I (compound of formula I-1, I-2, I-3), which comprise processes a) to c).

In particular embodiments of the present invention, the process a) includes, reacting compound of formula II:

[Chem.25]

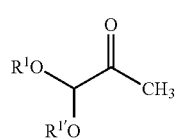

II wherein $R^1$ and $R^{1'}$ are defined above, with compound of formula III:

[Chem.26]

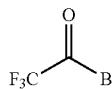

III wherein B is as defined above, in the present of DBU to obtain compound of formula I-1:

[Chem.27]

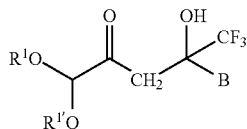

I-1 wherein $R^1$, $R^{1'}$, and B are as defined above.

<General Method of Process a)>

To mixture of compound of formula II and compound of formula III, DBU can be added as catalyst, and the reaction mixture can be stirred. Then, from the reaction mixture, compound of formula I can be obtained by methods known to the person skilled in the art, such as silica gel chromatography.

<Reaction Condition of Process a)>

In particular embodiments of the invention, in process a), the molar ratio of compound of formula II to compound of formula III is, for example, 1 to 20, preferably 2 to 10, more preferably 2 to 6.

In particular embodiments of the invention, in process a), the molar ratio of DBU to compound of formula III is, for example, 0.02 to 0.4, preferably 0.05 to 0.3, more preferably 0.05 to 0.2.

In particular embodiments of the invention, in process a), the reaction can be carried out in a solvent, which is not limited unless the solvent is involved in the reaction, such as toluene and 2-propanol, preferably the reaction is carried out without solvent.

In particular embodiments of the invention, in process a), the reaction time, which is not limited if compound of formula III is consumed, for example, 0.1 to 5 hours, preferably 0.2 to 3 hours, more preferably 0.3 to 2 hours when compound of formula I-1 contains no bulky group, OH and/or NH.

In particular embodiments of the invention, in process a), the reaction time, which is not limited if compound of formula III is consumed, for example, 0.1 to 96 hours, preferably 0.2 to 72 hours, more preferably 1 to 48 hours when compound of formula I-1 contains bulky group, OH and/or NH.

In particular embodiments of the invention, in process a), the reaction can be carried out, for example, at 10 to 60° C., preferably 15 to 50° C., more preferably 20 to 45° C.

In particular embodiments of the present invention, the process b) includes, reacting compound of formula IV:

[Chem.28]

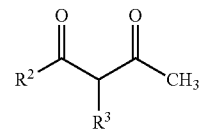

IV wherein $R^2$ and $R^3$ are as defined above, with compound of formula III:

[Chem.29]

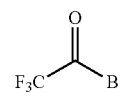

III wherein B is as defined above, in the presence of DBU to obtain compound of formula I-2:

[Chem.30]

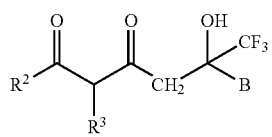

I-2 wherein $R^2$, $R^3$, and B are as defined above.

<General Method of Process b)>

To mixture of compound of formula IV (β-ketoester) and compound of formula III, DBU can be added as catalyst, and the reaction mixture can be stirred. Then, from the reaction mixture, compound of formula I-2 can be obtained by methods known to the person skilled in the art, such as silica gel chromatography.

<Reaction Condition of Process b)>

In particular embodiments of the invention, in process b), the molar ratio of compound of formula IV to compound of formula III is, for example, 1 to 20, preferably 2 to 10, more preferably 2 to 6.

In particular embodiments of the invention, in process b), the molar ratio of DBU to compound of formula III is, for example, 0.02 to 0.4, preferably 0.05 to 0.3, more preferably 0.05 to 0.2.

In particular embodiments of the invention, in process b), the reaction can be carried out in a solvent, which is not limited unless the solvent is involved in the reaction, such as toluene and 2-propanol, preferably the reaction is carried out without solvent.

In particular embodiments of the invention, in process b), the reaction time, which is not limited if compound of formula III is consumed, for example, 0.2 to 72 hours, preferably 1 to 48 hours, more preferably 2 to 30 hours.

In particular embodiments of the invention, in process b), the reaction can be carried out, for example, at 10 to 60° C., preferably 15 to 50° C., more preferably 20 to 45° C.

In particular embodiments of the present invention, the process c) includes, reacting compound of formula V:

[Chem.31]

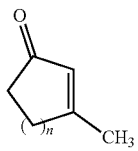

V wherein n is as defined above, with compound of formula III:

[Chem.32]

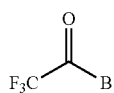

III wherein B is as defined above, in the presence of DBU to obtain compound of formula I-3:

[Chem.33]

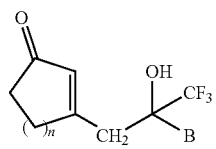

I-3 wherein B and n are as defined above.

<General Method of Process c)>

To mixture of compound of formula V (cyclic enone) and compound of formula III, DBU can be added as catalyst, and the reaction mixture can be stirred. Then, from the reaction mixture, compound of formula I-3 can be obtained by methods known to the person skilled in the art, such as silica gel chromatography.

<Reaction Condition of Process c)>

In particular embodiments of the invention, in process c), the molar ratio of compound of formula V to compound of formula III is, for example, 1 to 20, preferably 2 to 10, more preferably 2 to 6.

In particular embodiments of the invention, in process c), the molar ratio of DBU to compound of formula III is, for example, 0.02 to 0.4, preferably 0.05 to 0.3, more preferably 0.05 to 0.2.

In particular embodiments of the invention, in process c), the reaction can be carried out in a solvent, which is not limited unless the solvent is involved in the reaction, such as toluene and 2-propanol, preferably the reaction is carried out without solvent.

In particular embodiments of the invention, in process c), the reaction time, which is not limited if compound of formula III is consumed, for example, 0.1 to 24 hours, preferably 0.2 to 3 hours, more preferably 0.5 to 1 hours.

In particular embodiments of the invention, in process c), the reaction can be carried out, for example, at 10 to 60° C., preferably 15 to 50° C., more preferably 20 to 45° C.

Another aspects of the invention further include the methods for the preparation of compound of formula I-2 and I-2b, which comprises processes d) to f).

In particular embodiments of the present invention, the process d) includes, reacting compound of formula I-2:

[Chem.34]

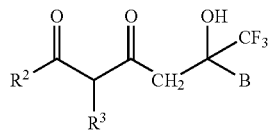

I-2 wherein $R^2$, $R^3$, and B are as define above, with a chiral amine:

[Chem.35]

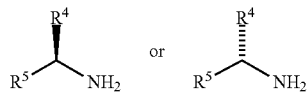

wherein $R^4$ and $R^5$ are independently each other selected from the group of $C_{1-7}$alkyl and phenyl optionally substituted with halogen, to obtain compound of formula I-2'-1:

[Chem.36]

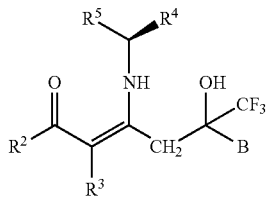

I-2'-1 wherein $R^2$, $R^3$, $R^4$, $R^5$, and B are as defined above, or compound of formula I-2'-2:

[Chem.37]

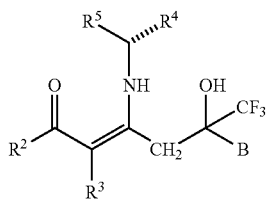

I-2'-2 wherein $R^2$, $R^3$, $R^4$, $R^5$, and B are as defined above.

<General Method of Process d)>

To the solution of compound of I-2 in a solvent such as toluene, chiral amine such as (R)-1-phenylethylamine can be added to obtain the mixture of compound of I-2'-1 and compound of formula I-2'-2. Then, the reaction mixture is purified by methods known to the person skilled in the art, such as chromatography to obtain compound of formula I-2'-1 or compound of formula I-2'-2.

<Reaction Condition of Process d)>

In particular embodiments of the invention, in process d), chiral amine can be used such as (R)-1-phenylethylamine, (S)-1-phenyl-ethylamine, (R)-1-(4-bromophenyl)ethylamine, (S)-1-(4-bromophenyl)ethylamine, and the like.

In particular embodiments of the invention, in process d), the molar ratio of chiral amine to compound of formula I-2 is, for example, 0.5 to 2.0, preferably 1.0 to 1.5, more preferably 1.0 to 1.2.

In particular embodiments of the invention, in process d), the reaction can be carried out in a solvent, which is not limited unless the solvent is involved in the reaction, such as toluene and $CH_2Cl_2$.

In particular embodiments of the invention, in process d), the reaction time, which is not limited if compound of formula I-2 is consumed, for example, 0.5 to 72 hours, preferably 1 to 48 hours, more preferably 2 to 12 hours.

In particular embodiments of the invention, in process d), the reaction can be carried out, for example, at 5 to 60° C., preferably 10 to 40° C., more preferably 15 to 30° C.

In particular embodiments of the present invention, the process e) includes, chiral resolution of compound of formula I-2'-1:

[Chem.38]

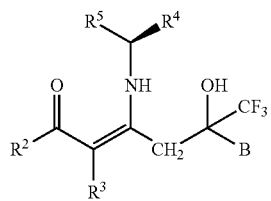

I-2'-1 wherein $R^2$, $R^3$, $R^4$, $R^5$, and B are as defined above, to obtain compound of formula I-2'-1-1:

[Chem.39]

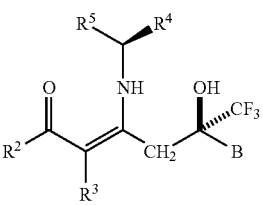

I-2'-1-1 wherein $R^2$, $R^3$, $R^4$, $R^5$, and B are as defined above, or compound of formula I-2'-1-2:

[Chem.40]

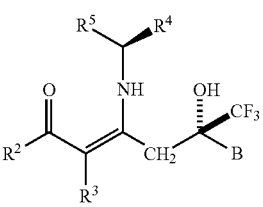

I-2'-1-2 wherein $R^2$, $R^3$, $R^4$, $R^5$, and B are as defined above.

<General Method of Process e)>

Diastereomeric resolution of compound of formula I-2'-1 or compound of formula I-2'-2 can be carried out by methods known to the person skilled in the art, such as chromatography, crystallization, and HPLC.

In particular embodiments of the present invention, the process f) includes, hydrolysis of compound of formula I-2'-1-1:

[Chem.41]

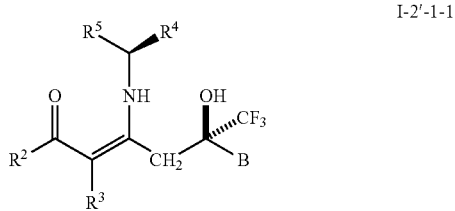

I-2'-1-1 wherein $R^2$, $R^3$, $R^4$, $R^5$, and B are as defined above, or compound of formula I-2'-1-2:

[Chem.42]

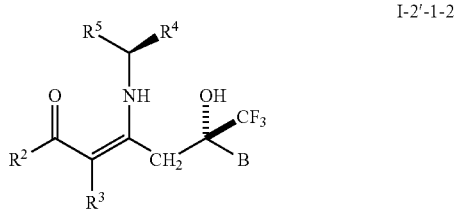

I-2'-1-2 wherein $R^2$, $R^3$, $R^4$, $R^5$, and B are as defined above, to obtain compound of formula I2a:

[Chem. 43]

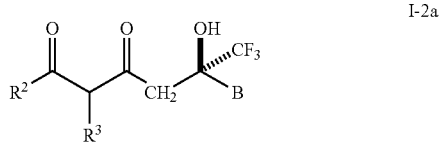

I-2a wherein $R^2$, $R^3$, and B are as defined above, or compound of formula I-2b:

[Chem. 44]

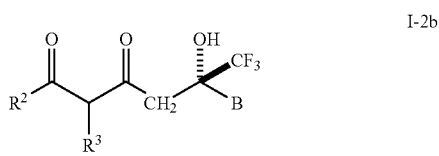

I-2b wherein $R^2$, $R^3$, and B are as defined above.

<General Method of Process f)>

Hydrolysis of compound of formula I-2'-1-1 and compound of formula of I-2'-1-1 can be carried out by methods known to the person skilled in the art, hydrolysis of enamines such as use of acid as catalyst. Hydrolysis of compound of formula I-2'-1-1 and compound of formula I-2'-1-2 provide corresponding compound of formula I-2a and compound of formula I-2b. The compounds, which are prepared from compound of formula I-2'-2 instead of compound of formula I-2'-1 in process e), can be used instead of compound of formula I-2'-1-1 and compound of formula I-2'-1-2.

<Reaction Condition of Process f)>

In particular embodiments of the invention, in process f), acidic catalyst can be used such as hydrochloric acid, phosphoric acid, and/or formic acid In particular embodiments of the invention, in process f), 5 to 25% solution of hydrochloric acid, preferably 10% solution of hydrochloric acid can be used.

In particular embodiments of the invention, in process f), the reaction can be carried out in a solvent, which is not limited unless the solvent is involved in the reaction, such as water-ethanol and water-isopropanol.

In particular embodiments of the invention, in process f), the reaction time, which is not limited if compound of formula I-2'-1-1 or compound of formula I-2'-1-2 is consumed, for example, 0.5 to 10 hours, preferably 1 to 5 hours, more preferably 1 to 4 hours. In case the reaction time is longer, decarboxylation reaction may occur.

In particular embodiments of the invention, in process f), the reaction can be carried out, for example, at 4 to 40° C., preferably 10 to 35° C., more preferably 15 to 30° C.

The invention further relates to the compound of formula I for use as a therapeutically active substance.

Pharmaceutical Compositions

The invention further relates to pharmaceutical composition comprising the compounds of formula I or pharmaceutically acceptable salts thereof, and pharmaceutically acceptable adjuvant.

The compounds of formula I as well as their pharmaceutically acceptable salts can be used as medicaments, e.g. in the form of pharmaceutical preparations. The pharmaceutical preparations can be administered orally, e.g. in the form of tablets, coated tablets, dragees, hard and soft capsules, solutions, emulsions or suspensions. The administration can however, also be effected rectally, e.g. in the form of suppositories, or parenterally, e.g. in the form of injection solutions.

The compounds of formula I and their pharmaceutically acceptable salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragees and hard gelatin capsules.

Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can be varied within wide limits and will, of course, be adapted to the individual requirements in each particular case. In general, in the case of oral administration a daily dosage of about 10 to 1000 mg per person of a compound of formula I should be appropriate, although the above upper limit may be exceeded when necessary.

EXAMPLES

The invention is illustrated hereinafter by Examples, which have no limiting character. In case the preparative examples are obtained as a mixture of enantiomers and diastereomers, the pure enantiomers or diastereomers may be separated by methods described herein or by methods known to the person skilled in the art, such as chiral chromatography and crystallization.

5,5,5-Trifluoro-4-hydroxy-1,1-dimethoxy-4-phenyl-pentan-2-one (3a)

[Chem. 45]

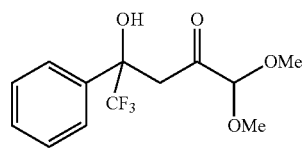

3a

<A General Synthetic Method of 3a>

To a mixture of 1,1-dimethoxyacetone (0.295 mL, 2.5 mmol) and phenyl trifluoromethyl ketone (70.2 μL, 0.5 mmol) was added DBU (7.45 μL, 0.05 mmol), and the mixture was stirred at RT (25° C.) until 1 was consumed (monitored by TLC), 1.5 h. The reaction mixture was diluted with hexane-EtOAc and purified by silica gel flash column chromatography (hexane/EtOAc=8:1 to 4:1) to give 3a (122.5 mg, 84%).

<A-Gram-Scale Reaction to Give 3a>

To a mixture of 1,1-dimethoxyacetone (2.95 mL, 25.0 mmol) and phenyl trifluoromethyl ketone (702 μL, 5.0 mmol) was added DBU (74.5 μL, 0.5 mmol), and the mixture was stirred at RT (25° C.) until 1 was consumed (monitored by TLC), 1.5 h. The reaction mixture was diluted with hexane-EtOAc and purified by silica gel flash column chromatography (hexane/EtOAc=8:1 to 4:1) to give 3a (1.38 g, 94%).

Colorless oil. $^1$H NMR (400 MHz, CDCl$_3$): δ=3.29 (d, J=17.8 Hz, 1H, CHHC=O), 3.30 (s, 3H, CH$_3$), 3.40 (s, 3H, OCH$_3$), 3.67 (d, J=17.8 Hz, 1H, CHHC=O), 4.29 (s, 1H, CH(OCH$_3$)$_2$), 5.01 (s, 1H, OH), 7.33-7.40 (m, 3H, ArH), 7.59 (dd, J=0.4 Hz, 7.5 Hz, 2H, ArH) ppm; $^{13}$C NMR (100 MHz, CDCl$_3$): δ=39.9, 55.21, 55.22, 76.0 (q, J$_{C,F}$=29 Hz), 104.4, 124.4 (q, J$_{C,F}$=283 Hz), 126.4, 128.3, 128.8, 137.1, 204.7 ppm; HRMS (ESI) calcd for C$_{13}$H$_{14}$O$_4$F$_3$ ([M−H]$^-$) 291.0839, found 291.0843.

Compounds 3b to 3 h were prepared according to the general synthetic method of compound 3a.

4-(4-Chlorophenyl)-5,5,5-trifluoro-4-hydroxy-1,1-dimethoxypentan-2-one (3b)

[Chem. 46]

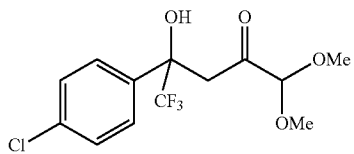

3b

Synthesized by the above general procedure, 1.0 h, 155.0 mg (95%).

Colorless oil. $^1$H NMR (400 MHz, CDCl$_3$): δ=3.28 (d, J=17.8 Hz, 1H, CHHC=O), 3.33 (s, 3H, OCH$_3$), 3.42 (s, 3H, OCH$_3$), 3.60 (d, J=17.8 Hz, 1H, CHHC=O), 4.27 (s, 1H, CH(OCH$_3$)$_2$), 5.02 (s, 1H, OH), 7.33-7.37 (m, 2H, ArH), 7.52 (d, J=8.5 Hz, 2H, ArH) ppm; $^{13}$C NMR (100 MHz, CDCl$_3$): δ=39.6, 55.4, 55.5, 75.8 (q, $J_{C,F}$=30 Hz), 104.5, 124.2 (q, $J_{C,F}$=283 Hz), 128.0, 128.5, 135.0, 135.7, 204.5 ppm; HRMS (ESI) calcd for C$_{13}$H$_{13}$O$_4$F$_3$Cl ([M−H]$^-$) 325.0449, found 329.0458.

4-(4-Bromophenyl)-5,5,5-trifluoro-4-hydroxy-1,1-dimethoxypentan-2-one (3c)

[Chem. 47]

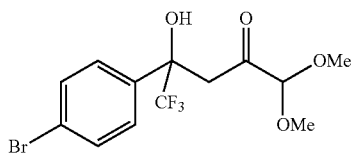

3c

Synthesized by the above general procedure, 1.0 h, 159.4 mg (86%).

Colorless oil. $^1$H NMR (400 MHz, CDCl$_3$): δ=3.27 (d, J=17.8 Hz, 1H, CHHC=O), 3.32 (s, 3H, OCH$_3$), 3.41 (s, 3H, OCH$_3$), 3.60 (d, J=17.8 Hz, 1H, CHHC=O), 4.27 (s, 1H, CH(OCH$_3$)$_2$), 5.03 (s, 1H, OH), 7.46 (d, J=8.5 Hz, 2H, ArH), 7.49-7.52 (m, 2H, ArH) ppm; $^{13}$C NMR (100 MHz, CDCl$_3$): δ=39.5, 55.37, 55.42, 75.8 (q, $J_{C,F}$=29 Hz), 104.4, 123.2, 124.1 (q, $J_{C,F}$=283 Hz), 128.3, 131.4, 136.3, 204.4 ppm; HRMS (ESI) calcd for C$_{13}$H$_{13}$O$_4$F$_3$Br ([M−H]$^-$) 368.9944, found 368.9975.

5,5,5-Trifluoro-4-hydroxy-1,1-dimethoxy-4-(4-(trifluoromethyl)phenyl)pentan-2-one (3d)

[Chem. 48]

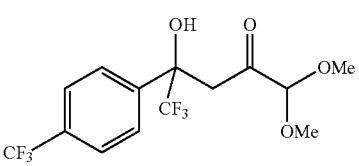

3d

Synthesized by the above general procedure, 1.0 h, 156.4 mg (87%).

Colorless oil. $^1$H NMR (400 MHz, CDCl$_3$): δ=3.32 (s, 3H, OCH$_3$), 3.34 (d, J=17.8 Hz, 1H, CHHC=O), 3.42 (s, 3H, OCH$_3$), 3.64 (d, J=17.8 Hz, 1H, CHHC=O), 4.28 (s, 1H, CH(OCH$_3$)$_2$), 5.12 (s, 1H, OH), 7.64 (d, J=8.4 Hz, 2H, ArH), 7.73 (d, J=8.4 Hz, 2H, ArH) ppm; $^{13}$C NMR (100 MHz, CDCl$_3$): δ=39.6, 55.4, 55.5, 75.9 (q, $J_{C,F}$=29 Hz), 104.5, 123.9 (q, $J_{C,F}$=271 Hz), 124.1 (q, $J_{C,F}$=283 Hz), 125.2 (q, $J_{C,F}$=4.0 Hz), 127.1, 131.0 (q, $J_{C,F}$=32 Hz), 141.2, 204.4 ppm; HRMS (ESI) calcd for C$_{14}$H$_{13}$O$_4$F$_6$ ([M−H]$^-$) 359.0713, found 359.0716.

5,5,5-Trifluoro-4-hydroxy-1,1-dimethoxy-4-(p-tolyl)pentan-2-one (3e)

[Chem. 49]

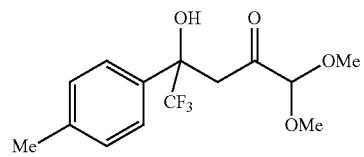

3e

Synthesized by the above general procedure, 1.5 h, 139.3 mg (91%).

Colorless oil. $^1$H NMR (400 MHz, CDCl$_3$): δ=2.34 (s, 3H, ArCH$_3$) 3.27 (d, J=17.8 Hz, 1H, CHHC=O), 3.32 (s, 3H, OCH$_3$), 3.40 (s, 3H, OCH$_3$) 3.66 (d, J=17.8 Hz, 1H, CHHC=O), 4.29 (s, 1H, CH(OCH$_3$)$_2$), 4.95 (s, 1H, OH), 7.19 (d, J=8.0 Hz, 2H, ArH), 7.47 (d, J=8.0 Hz, 2H, ArH) ppm; $^{13}$C NMR (100 MHz, CDCl$_3$): δ=20.9, 39.8, 55.15, 55.20, 75.9 (q, $J_{C,F}$=29 Hz), 104.3, 124.4 (q, $J_{C,F}$=283 Hz), 126.3, 129.0, 134.1, 138.6, 204.8 ppm; HRMS (ESI) calcd for C$_{14}$H$_{16}$O$_4$F$_3$ ([M−H]$^-$) 305.0995, found 305.0994.

5,5,5-Trifluoro-4-hydroxy-1,1-dimethoxy-4-(4-methoxyphenyl)pentan-2-one (3f)

[Chem. 50]

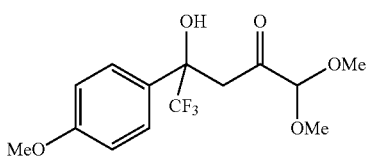

3f

Synthesized by the above general procedure, 1.5 h, 143.3 mg (89%).

Colorless oil. $^1$H NMR (400 MHz, CDCl$_3$): δ=3.24 (d, J=17.8 Hz, 1H, CHHC=O), 3.32 (s, 3H, OCH$_3$), 3.40 (s, 3H, OCH$_3$), 3.64 (d, J=17.8 Hz, 1H, CHHC=O), 3.80 (s, 3H, OCH$_3$), 4.28 (s, 1H, CH(OCH$_3$)$_2$), 4.95 (s, 1H, OH), 6.87-6.91 (m, 2H, ArH), 7.50 (d, J=8.8 Hz, 2H, ArH) ppm; $^{13}$C NMR (100 MHz, CDCl$_3$): δ=39.8, 55.13, 55.18, 55.23, 75.8 (q, $J_{C,F}$=29 Hz), 104.4, 113.6, 124.4 (q, $J_{C,F}$=283 Hz), 127.7, 129.0, 159.9, 204.7 ppm; HRMS (ESI) calcd for C$_{14}$H$_{16}$O$_5$F$_3$ ([M−H]$^-$) 321.0944, found 321.0946.

5,5,5-Trifluoro-4-hydroxy-1,1-dimethoxy-4-(thiophen-2-yl)pentan-2-one (3g)

[Chem. 51]

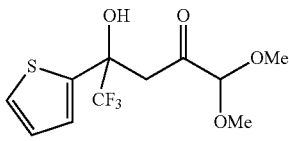

3g

Synthesized by the above general procedure, 1.5 h, 129.7 mg (87%).

Colorless oil. $^1$H NMR (400 MHz, CDCl$_3$): δ=3.26 (d, J=17.7 Hz, 1H, CHHC=O), 3.34 (s, 3H, OCH$_3$), 3.41 (s, 3H, OCH$_3$), 3.58 (d, J=17.7 Hz, 1H, CHHC=O), 4.32 (s, 1H, CH(OCH$_3$)$_2$), 5.45 (s, 1H, OH), 6.99 (dd, J=3.6 Hz, 5.1 Hz, 1H, ArH), 7.10 (d, J=3.6 Hz, 1H, ArH), 7.32 (dd, J=1.2 Hz, 5.1 Hz, 1H, ArH) ppm; $^{13}$C NMR (100 MHz, CDCl$_3$): δ=40.6, 55.2, 55.3, 75.4 (q, $J_{C,F}$=31 Hz), 104.3, 123.7 (q, $J_{C,F}$=283 Hz), 126.0, 126.6, 127.0, 141.4, 204.5 ppm; HRMS (ESI) calcd for C$_{11}$H$_{12}$O$_4$F$_3$S ([M−H]$^-$) 297.0403, found 297.0417.

3-(Dimethoxymethyl)-1-(trifluoromethyl)-2,3-dihydro-1H-pyrrolizine-1,3-diol (3h)

[Chem. 52]

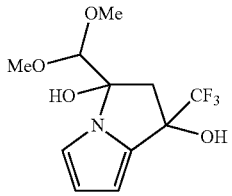

3h

Synthesized by the above general procedure using DBU (0.1 mmol, 0.2 equiv), 48 h.

Upper spot on TLC, Rf=0.34 (hexane/EtOAc=2:1): 3 h-1 (50.5 mg, 36%)

Colorless oil. $^1$H NMR (400 MHz, CDCl$_3$): δ=2.87 (d, J=14.8 Hz, 1H, CHHC=O), 2.94 (d, J=14.8 Hz, 1H, CHHC=O), 3.32 (s, 3H, OCH$_3$), 3.52 (s, 3H, OCH$_3$), 3.50-3.70 (br, 2H, OH), 4.41 (s, 1H, CH(OCH$_3$)$_2$), 6.16 (d, J=3.2 Hz, 1H, ArH), 6.33 (t, J=3.2 Hz, 1H, ArH), 6.80 (m, 1H, ArH) ppm; $^{13}$C NMR (100 MHz, CDCl$_3$): δ=48.4, 57.2, 58.3, 74.6 (q, $J_{C,F}$=32 Hz), 89.7, 102.4, 106.9, 113.7, 114.9, 124.5 (q, $J_{C,F}$=289 Hz), 132.9 ppm; HRMS (ESI) calcd for C$_{11}$H$_{15}$NO$_4$F$_3$ ([M+H]$^+$) 282.0948, found 282.0949.

Lower spot on TLC, Rf=0.23 (hexane/EtOAc=2:1): 3 h-2 (63.1 mg, 45%)

Colorless oil. 1H NMR (400 MHz, CDCl$_3$): δ=2.48 (d, J=14.8 Hz, 1H, CHHC=O), 3.20 (d, J=14.8 Hz, 1H, CHHC=O), 3.49 (s, 3H, OCH$_3$), 3.52 (s, 3H, OCH$^3$), 4.09 (br, 1H, OH), 4.44 (s, 1H, CH(OCH$_3$)$_2$), 6.12 (d, J=3.2 Hz, 1H, ArH), 6.29 (t, J=3.2 Hz, 1H, ArH), 6.81-6.82 (m, 1H, ArH) ppm; $^{13}$C NMR (100 MHz, CDCl$_3$): δ=47.5, 56.85, 56.99, 74.8 (q, JC,F=32 Hz), 89.4, 102.3, 105.3, 114.70, 114.72, 124.5 (q, JC,F=280 Hz), 133.1 ppm; HRMS (ESI) calcd for C$_{11}$H$_{15}$NO$_4$F$_3$ ([M+H]$^+$) 282.0948, found 282.0947.

Ethyl 6,6,6-trifluoro-5-hydroxy-3-oxo-5-phenylhexanoate (4a)

[Chem. 53]

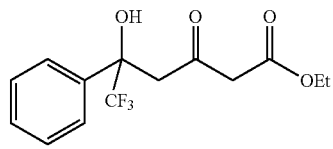

4a

<A General Synthetic Method of 4a>

To a mixture of ethyl acetoacetate (5.0 mmol) and phenyl trifluoromethyl ketone (0.5 mmol) was added DBU (0.1 mmol), and the mixture was stirred at RT (25° C.) until 1 was consumed (monitored by TLC), 24 h. The reaction mixture was diluted with hexane-EtOAc and purified by silica gel flash column chromatography (hexane/EtOAc=8:1 to 4:1) to give 4a (126.0 mg, 83%).

<A 15 mmol-Scale Reaction to Give 4a>

To a mixture of ethyl acetoacetate (9.48 mL, 75.0 mmol, 5.0 equiv) and 1a (2.11 mL, 15.0 mmol, 1.0 equiv) was added DBU (224 μL, 1.50 mmol, 0.1 equiv), and the mixture was stirred at RT (25° C.) for 4 days. The reaction mixture was diluted with hexane-EtOAc and purified by silica gel flash column chromatography (hexane/EtOAc=15:1 to 8:1) to give 4a (3.29 g, 72%).

Compounds 4aa to 4ac and 4b, 4ba to 4bc were prepared according to the synthetic method of compound 3a.

Ethyl 6,6,6-trifluoro-5-hydroxy-5-(4-methoxyphenyl)-3-oxohexanoate (4aa)

[Chem. 54]

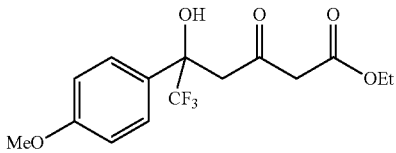

4aa

Synthesized by the above general procedure, 36 h, 105.3 mg (63%).

Colorless oil. $^1$H NMR (400 MHz, CDCl$_3$): δ=1.26 (t, J=7.2 Hz, 3H, OCH$_2$CH$_3$), 3.31 (d, J=17.6 Hz, 1H, C(OH)CHHC=O), 3.40 (d, J=15.6 Hz, 1H, C(=O)CH HCOOEt), 3.44 (d, J=15.6 Hz, 1H, C(=O)CHHCOOEt), 3.56 (d, J=17.6 Hz, 1H, C(OH)CHHC=O), 3.80 (s, 3H, OCH$_3$) 4.19 (q, J=7.2 Hz, 2H, OCH$_2$CH$_3$), 4.92 (brs, 1H, OH), 6.90 (d, J=8.8 Hz, 2H, ArH), 7.48 (d, J=8.8 Hz, 2H, ArH) ppm; $^{13}$C NMR (100 MHz, CDCl$_3$): δ=13.9, 45.2, 50.5, 55.2, 61.8, 75.7 (q, $J_{C,F}$=29 Hz), 113.8 124.4 (q, $J_{C,F}$=283 Hz), 127.5, 128.7, 159.9, 166.2, 202.5 ppm; HRMS (ESI) calcd for C$_{15}$H$_{16}$O$_5$F$_3$ ([M+H]$^+$) 335.1101, found 335.1088.

Ethyl 5-(4-chlorophenyl)-6,6,6-trifluoro-5-hydroxy-3-oxohexanoate (4ab)

[Chem. 55]

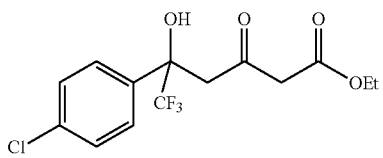
4ab

Synthesized by the above general procedure, 24 h, 131.5 mg (78%).

Colorless oil. $^1$H NMR (400 MHz, CDCl$_3$): δ=1.26 (t, J=7.2 Hz, 3H, OCH$_2$CH$_3$), 3.35 (d, J=17.6 Hz, 1H, C(OH)CHHC=O), 3.41 (d, J=15.6 Hz, 1H, C(=O)CH HCOOEt), 3.46 (d, J=15.6 Hz, 1H, C(=O)CHHCOOEt), 3.56 (d, J=17.6 Hz, 1H, C(OH)CHHC=O), 4.19 (q, J=7.2 Hz, 2H, OCH$_2$CH$_3$), 5.04 (s, 1H, OH), 7.36 (d, J=8.4 Hz, 2H, ArH), 7.51 (d, J=8.4 Hz, 2H, ArH) ppm; $^{13}$C NMR (100 MHz, CDCl$_3$): δ=13.9, 45.0, 50.4, 62.0, 75.7 (q, J$_{C,F}$=29 Hz), 124.1 (q, J$_{C,F}$=283 Hz), 127.7, 128.7, 135.1, 135.5, 166.2, 202.3 ppm; HRMS (ESI) calcd for C$_{14}$H$_{15}$O$_4$F$_3$Cl ([M+H]$^+$) 339.0605, found 339.0591.

Ethyl 6,6,6-trifluoro-5-hydroxy-3-oxo-5-(thiophen-2-yl)hexanoate (4ac)

[Chem. 56]

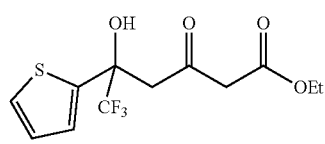
4ac

Synthesized by the above general procedure, 24 h, 130.4 mg (84%).

Colorless oil. $^1$H NMR (400 MHz, CDCl$_3$): δ=1.26 (t, J=7.2 Hz, 3H, OCH$_2$CH$_3$), 3.32 (d, J=17.2 Hz, 1H, C(OH)CHHC=O), 3.46 (s, 2H, C(=O)CH$_2$COOEt), 3.52 (d, J=17.6 Hz, 1H, C(OH)CHHC=O), 4.19 (q, J=7.2 Hz, 2H, OCH$_2$CH$_3$), 5.42 (s, 1H, OH), 6.99-7.01 (m, 2H, ArH), 7.32-7.34 (m, 2H, ArH) ppm; $^{13}$C NMR (100 MHz, CDCl$_3$): δ=13.9, 45.8, 50.5, 61.9, 75.3 (q, J$_{C,F}$=31 Hz), 123.7 (q, J$_{C,F}$=283 Hz), 126.0, 126.7, 127.2, 141.0, 166.1, 202.4 ppm; HRMS (ESI) calcd for C$_{12}$H$_{14}$O$_4$F$_3$S ([M+H]$^+$) 311.0559, found 311.0549.

Ethyl 6,6,6-trifluoro-5-hydroxy-2-methyl-3-oxo-5-phenylhexanoate (4b)

[Chem. 57]

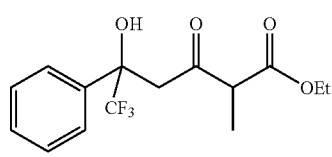
4b

Synthesized by the above general procedure, 24 h, 127.5 mg (80%).

Colorless oil. $^1$H NMR (400 MHz, CDCl$_3$): δ=1.22-1.29 (m, 6H, OCH$_2$CH$_3$, CH$_3$CHC=O), 3.31-3.61 (m, 3H, CH$_3$CHC=O, C(OH)CH$_2$C=O), 4.11-4.24 (m, 2H, OCH$_2$CH$_3$), 5.20 (brs, 1H×½, OH), 5.24 (brs, 1H×½, OH) 7.33-7.41 (m, 3H, ArH), 7.56-7.57 (m, 2H, ArH) ppm; $^{13}$C NMR (100 MHz, CDCl$_3$): δ=12.1, 12.2, 13.9, 43.8, 44.0, 53.9, 54.4, 61.8, 61.9, 75.69 (q, J$_{C,F}$=29 Hz), 76.01 (q, J$_{C,F}$=29 Hz), 124.37 (q, J$_{C,F}$=283 Hz), 124.44 (q, J$_{C,F}$=283 Hz), 126.05, 126.09, 128.3, 128.4, 128.79, 128.83, 137.05, 137.16, 169.21, 169.23, 205.7, 206.0 ppm; HRMS (ESI) calcd for C$_{15}$H$_{18}$O$_4$F$_3$ ([M+H]$^+$) 319.1152, found 319.1135.

Ethyl 6,6,6-trifluoro-5-hydroxy-5-(4-methoxyphenyl)-2-methyl-3-oxohexanoate (4ba)

[Chem. 58]

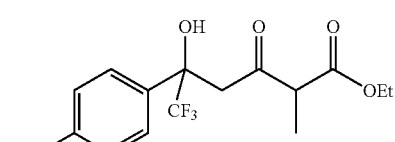
4ba

Synthesized by the above general procedure, 26 h, 115.3 mg (66%).

Colorless oil. $^1$H NMR (400 MHz, CDCl$_3$): δ=1.23-1.29 (m, 6H, OCH$_2$CH$_3$, CH$_3$CHC=O), 3.27-3.59 (m, 3H, CH$_3$CHC=O, C(OH)CH$_2$C=O), 3.79 (s, 3H×½, OCH$_3$), 3.80 (s, 3H×½, OCH$_3$), 4.13-4.23 (m, 2H, OCH$_2$CH$_3$), 5.08 (brs, 1H×½, OH), 5.16 (brs, 1H×½, OH), 6.87-6.92 (m, 2H, ArH), 7.45-7.47 (m, 2H, ArH) ppm; $^{13}$C NMR (100 MHz, CDCl$_3$): δ=12.1, 12.2, 13.9, 43.7, 44.0, 53.9, 54.4, 55.2, 61.8, 61.9, 75.7 (q, J$_{C,F}$=29 Hz), 75.8 (q, J$_{C,F}$=29 Hz), 113.7, 113.8, 124.4 (q, J$_{C,F}$=283 Hz), 124.5 (q, J$_{C,F}$=283 Hz), 127.39, 127.44, 129.0, 129.1, 159.87, 159.88, 169.29, 169.30, 205.7, 206.1 ppm; HRMS (ESI) calcd for C$_{16}$H$_{20}$O$_5$F$_3$ ([M+H]$^+$) 349.1257, found 349.1250.

Ethyl 5-(4-chlorophenyl)-6,6,6-trifluoro-5-hydroxy-2-methyl-3-oxohexanoate (4bb)

[Chem. 59]

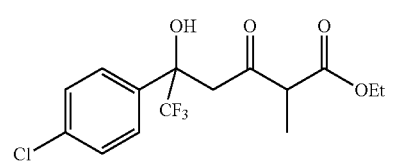
4bb

Synthesized by the above general procedure, 24 h, 132.3 mg (75%).

Colorless oil. $^1$H NMR (400 MHz, CDCl$_3$): δ=1.22-1.29 (m, 6H, OCH$_2$CH$_3$, CH$_3$CHC=O), 3.28-3.59 (m, 3H, CH$_3$CHC=O, C(OH)CH$_2$C=O), 4.12-4.23 (m, 2H, OCH$_2$CH$_3$), 5.17 (brs, 1H×½, OH), 5.28 (brs, 1H×½, OH), 7.33-7.37 (m, 2H, ArH), 7.48-7.50 (m, 2H, ArH) ppm; $^{13}$C NMR (100 MHz, CDCl$_3$): δ=12.1, 12.2, 13.88, 13.89, 43.5, 43.9, 53.8, 54.3, 61.9, 62.0, 75.73 (q, J$_{C,F}$=29 Hz), 75.74 (q, $J_{C,F}$=29 Hz), 124.17 (q, $J_{C,F}$=283 Hz), 124.20 (q, $J_{C,F}$=283 Hz), 127.6, 127.7, 128.5, 128.6, 135.00, 135.03 135.7, 135.8, 169.21, 169.22, 205.6, 205.8 ppm; HRMS (ESI) calcd for $C_{15}H_{17}O_4F_3Cl$ ([M+H]$^+$) 353.0762, found 353.0747.

Ethyl 6,6,6-trifluoro-5-hydroxy-2-methyl-3-oxo-5-(thiophen-2-yl)hexanoate (4bc)

[Chem. 60]

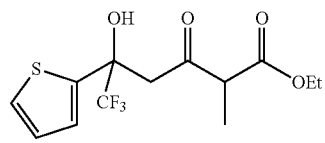

4bc

Synthesized by the general procedure, 26 h, 113.5 mg (70%).

Colorless oil. $^1$H NMR (400 MHz, CDCl$_3$): δ=1.23-1.31 (m, 6H, OCH$_2$CH$_3$, CH$_3$CHC=O), 3.27-3.60 (m, 3H, CH$_3$CHC=O, C(OH)CH$_2$C=O), 4.13-4.23 (m, 2H, OCH$_2$CH$_3$), 5.59 (brs, 1H×½, OH), 5.62 (brs, 1H×½, OH), 6.98-7.01 (m, 1H, ArH), 7.07-7.10 (m, 1H, ArH), 7.32-7.33 (m, 1H, ArH) ppm; $^{13}$C NMR (100 MHz, CDCl$_3$): δ=12.1, 12.2, 13.9, 44.5, 44.6, 54.0, 54.4, 61.8, 61.9, 75.41 (q, $J_{C,F}$=30 Hz), 75.44 (q, $J_{C,F}$=31 Hz), 123.7 (q, $J_{C,F}$=283 Hz), 123.8 (q, $J_{C,F}$=283 Hz), 125.7, 125.8, 126.5, 126.6, 127.1, 127.2, 141.2, 141.3, 169.12, 169.15, 205.6, 206.0 ppm; HRMS (ESI) calcd for $C_{13}H_{16}O_4F_3S$ ([M+H]$^+$) 325.0716, found 325.0703.

Synthesis of Compound 5a-1: (R)-ethyl 6,6,6,-trifluoro-5-hydroxy-5-phenyl-(((R)-1-phenyl)amino)hex-2-enoate

[Chem. 61]

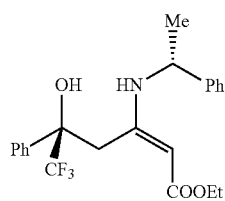

5a-1

Synthesis of Compound 5a-1: (S)-ethyl 6,6,6,-trifluoro-5-hydroxy-5-phenyl-(((R)-1-phenyl)amino)hex-2-enoate

[Chem. 62]

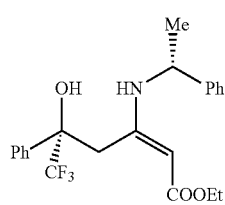

5a-2

To a solution of 4a (243.4 mg, 0.8 mmol) in toluene (1.5 mL), (R)-1-phenylethylamine (112 µL, 0.88 mmol) was added, and the mixture was stirred at RT (25° C.) for 12 h. The mixture was purified by silica gel flash column chromatography (hexane/EtOAc=30:1 to 15:1) to give 5a-1 (upper spot on TLC) (108.5 mg, 32%, dr 20:1), mixtures of 5a-1 and 5a-2 (81.7 mg, 24%, dr 1:1), and 5a-2 (lower spot on TLC) (105.5 mg, 31%, dr 20:1); the dr values of 5a-1 and 5a-2 were determined by $^1$H NMR analyses. Compound 5a-1 (dr 20:1) was crystallized from hexane-CH$_2$Cl$_2$ to give the essentially pure form (50.5 mg, dr>99:1). Compound 5a-2 (dr 20:1) was also crystallized from hexane-CH2Cl2 to increase the purity (60.0 mg, dr 99:1). The absolute stereochemistry of 5a-1 was determined to be (R,R) by the X-ray structural analysis. Note that the fractions containing 5a-1 and 5a-2 were able to be purified further to give pure 5a-1 and also pure 5a-2.

Compound 5a-1: Colorless crystals, mp 126° C., $R_f$=0.38 (hexane/EtOAc=10:1). $^1$H NMR (400 MHz, CDCl$_3$): δ=0.67 (d, J=6.4 Hz, 3H, NCH(CH$_3$)Ph), 1.13 (t, J=7.2 Hz, 3H, OCH$_2$CH$_3$), 2.58 (d, J=13.6 Hz, 1H, C(OH)CHH), 3.52 (d, J=5.6 Hz, 1H, C=CHCOOEt), 3.87-4.10 (m, 3H, NCH(CH$_3$)Ph, OCH$_2$CH$_3$), 4.16 (d, J=13.6 Hz, 1H, C(OH)CHH), 4.49 (s, 1H, OH), 6.89-6.91 (m, 3H, ArH, NH), 7.12-7.21 (m, 3H, ArH), 7.32-7.41 (m, 3H, ArH), 7.65-7.67 (m, 2H, ArH) ppm; $^{13}$C NMR (100 MHz, CDCl$_3$): δ=14.4, 22.2, 38.7, 53.1, 59.9, 76.8 (q, $J_{C,F}$=25 Hz), 87.6, 125.4, 125.8 (q, $J_{C,F}$=285 Hz), 126.1, 127.5, 128.6, 128.77, 128.80, 137.8, 142.4, 155.2, 172.2 ppm; HRMS (ESI) calcd for $C_{22}H_{25}NO_3F_3$ ([M+H]$^+$) 408.1781, found 408.1762.

Compound 5a-2: Colorless solid, $R_f$=0.28 (hexane/EtOAc=10:1). $^1$H NMR (400 MHz, CDCl$_3$): δ=1.20-1.24 (m, 6H, NCH(CH$_3$)Ph, OCH$_2$CH$_3$), 2.80 (d, J=13.6 Hz, 1H, C(OH)CHH), 3.85 (d, J=5.6 Hz, 1H, C=CHCOOEt), 4.04-4.23 (m, 4H, NCH(CH$_3$)Ph, OCH$_2$CH$_3$, C(OH)CHH), 4.55 (s, 1H, OH), 6.49-6.51 (m, 2H, ArH), 6.94 (s, 1H, NH), 7.15-7.17 (m, 3H, ArH), 7.36-7.46 (m, 4H, ArH), 7.70-7.72 (m, 2H, ArH) ppm; $^{13}$C NMR (100 MHz, CDCl$_3$): δ=14.4, 23.4, 38.5, 52.9, 60.0, 76.8 (q, $J_{C,F}$=28 Hz), 87.8, 125.4, 125.7 (q, $J_{C,F}$=286 Hz) 126.4, 127.2, 128.5, 128.5, 128.6, 128.7, 137.4, 141.9, 154.5, 172.1 ppm; HRMS (ESI) calcd for $C_{22}H_{25}NO_3F_3$ ([M+H]$^+$) 408.1781, found 408.1762.

Compounds 5ac-1 and 5ac-2 were prepared according to the synthetic method of compound 5a-1 and 5a-2.

Compound 5ac-1: (S)-ethyl 6,6,6-trifluoro-5-hydroxy-3-(((R)-1-phenylethyl)amino)-5-(thiophen-2-yl)hexa-2-enoate

[Chem. 63]

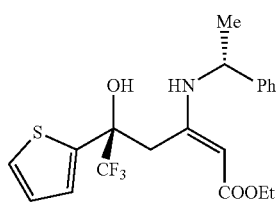

5ac-1

Crystallized from hexane-CH$_2$Cl$_2$, colorless crystals, mp 133° C., $R_f$=0.33 (hexane/EtOAc=10:1). $^1$H NMR (400 MHz, CDCl$_3$): δ=0.86 (d, J=6.8 Hz, 3H, NCH(CH$_3$)Ph), 1.13 (t, J=7.2 Hz, 3H, OCH$_2$CH$_3$), 2.45 (d, J=13.2 Hz, 1H, C(OH)C HH), 3.75 (d, J=5.2 Hz, 1H, C=CHCOOEt), 3.93-4.09 (m, 3H, NCH(CH₃)Ph, OCH₂CH₃), 4.16 (d, J=13.2 Hz, 1H, C(OH)CHH), 4.53 (s, 1H, OH), 6.96-7.05 (m, 3H, ArH), 7.13-7.18 (m, 2H, ArH), 7.23-7.26 (m, 2H, ArH), 7.30-7.31 (m, 1H, ArH), 7.38 (s, 1H, NH) ppm; $^{13}$C NMR (100 MHz, CDCl₃): δ=14.3, 22.6, 40.1, 53.4, 60.1, 76.8 (q, $J_{C,F}$=30 Hz), 87.8, 123.8, 125.1 (q, $J_{C,F}$=285 Hz), 125.5, 126.1, 127.5, 127.6, 128.9, 142.4, 143.2, 155.0, 172.4 ppm; HRMS (ESI) calcd for $C_{20}H_{23}NO_3F_3S$ ([M+H]$^+$) 414.1345, found 414.1327.

Compound 5ac-2: (R)-ethyl 6,6,6-trifluoro-5-hydroxy-3-(((R)-1-phenylethyl)amino)-5-(thiophen-2-yl)hexa-2-enoate

[Chem. 64]

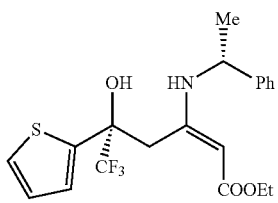

5ac-2

Crystallized from hexane-CH₂Cl₂, colorless crystals, $R_f$=0.24 (hexane/EtOAc=10:1). $^1$H NMR (400 MHz, CDCl₃): δ=1.23 (t, J=7.0 Hz, 3H, OCH₂CH₃), 1.31 (d, J=6.8 Hz, 3H, NCH(CH₃)Ph), 2.68 (d, J=13.6 Hz, 1H, C(OH)CHH), 4.03-4.27 (m, 5H, NCH(CH₃)Ph, OCH₂CH₃, C(OH)CHH, C=CHCOOEt), 4.64 (s, 1H, OH), 6.69-6.72 (m, 2H, ArH), 7.00-7.02 (m, 1H, ArH), 7.17-7.26 (m, 4H, ArH), 7.29-7.31 (m, 1H, ArH), 7.41 (s, 1H, NH) ppm; $^{13}$C NMR (100 MHz, CDCl₃): δ=14.3, 23.1, 40.0, 53.2, 60.1, 76.7 (q, $J_{C,F}$=29 Hz), 87.6, 124.5, 125.0 (q, $J_{C,F}$=285 Hz), 125.6, 126.2, 127.3, 128.6, 141.9, 142.3, 154.2, 172.3 ppm; HRMS (ESI) calcd for $C_{20}H_{23}NO_3F_3S$ ([M+H]$^+$) 414.1345, found 414.1327.

Synthesis of compound (R)-4a: (R)-ethyl 6,6,6-trifluoro-5-hydroxy-3-oxo-5-phenylhexanoate

[Chem. 65]

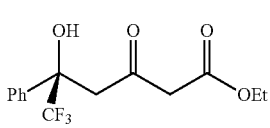

(R)-4a

A mixture of 5a-1 (0.12 mmol, 50.0 mg, dr>99:1) and 10% HCl/(H₂O/EtOH=1:1) (1.0 mL) was stirred at RT (25° C.) for 4 h. The reaction mixture was extracted with CH₂Cl₂ (3 mL×3). Organic layers were combined, washed with brine, dried over MgSO₄, concentrated, and purified by flash column chromatography (hexane/EtOAc=5:1) to give (R)-4a (31.5 mg, 89%, >99%). The ee value was determined by HPLC analysis.

Colorless oil. $[\alpha]_D^{26}$-34.2 (c=0.67, CH₂Cl₂), >99% ee. HPLC (Daicel Chiralpak IA, hexane/2-PrOH=98:2, 0.6 mL/min, λ=254 nm): $t_R$ (major, (R)-4a)=27.9 min, $t_R$(miner, (S)-4a)=31.8 min.

Compounds (S)-4a, (S)-4ac, and (R)-4ac were prepared according to the synthetic method of compound (R)-4a.

Compound (S)-4a: (S)-ethyl 6,6,6-trifluoro-5-hydroxy-3-oxo-5-phenylhexanoate

[Chem. 66]

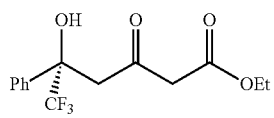

(S)-4a

Colorless oil. $[\alpha]_D^{26}$+30.5 (c=0.37, CH2Cl2), 98% ee. HPLC (Daicel Chiralpak IA, hexane/2-PrOH=98:2, 0.6 mL/min, λ=254 nm): $t_R$ (miner, (R)-4a)=27.8 min, $t_R$(major, (S)-4a)=31.6 min.

Compound (S)-4ac: (S)-Ethyl 6,6,6-trifluoro-5-hydroxy-3-oxo-5-(thiophen-2-yl)hexanoate

[Chem. 67]

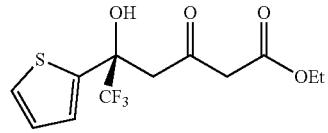

(S)-4ac

Colorless oil. $[\alpha]_D^{25}$-40.9 (c=0.53, CH₂Cl₂), 99.8% ee. HPLC (Daicel Chiralpak AS, hexane/2-PrOH=98:2, 0.6 mL/min, λ=254 nm): $t_R$ (major, (S)-4ac)=39.7 min, $t_R$(miner, (R)-4ac)=53.0 min.

Compound (R)-4ac: (R)-Ethyl 6,6,6-trifluoro-5-hydroxy-3-oxo-5-(thiophen-2-yl)hexanoate

[Chem. 68]

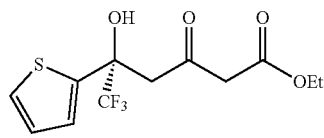

(R)-4ac

Colorless oil. $[\alpha]_D^{25}$+40.5 (c=0.74, CH2Cl2), >99% ee. HPLC (Daicel Chiralpak AS, hexane/2-PrOH=98:2, 0.6 mL/min, λ=254 nm): $t_R$ (miner, (S)-4ac)=40.8 min, $t_R$(major, (R)-4ac)=50.5 min

Synthesis of 3-(3,3,3-Trifluoro-2-hydroxy-2-phenyl-propyl)cyclohex-2-enone (8a)

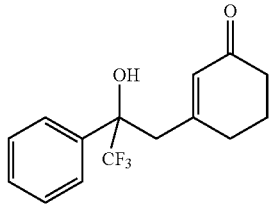

To a mixture of 3-methyl-2-cyclohexenone (2.5 mmol) and phenyl trifluoroketone (0.5 mmol) was added DBU (0.05 mmol), and the mixture was stirred at RT (25° C.) until phenyl trifluoroketone was consumed (monitored by TLC), 1.0 h. The reaction mixture was diluted with hexane-EtOAc and purified by silica gel flash column chromatography (hexane/EtOAc=8:1 to 4:1) to give 8a (81%).

Colorless solid. $^1$H NMR (400 MHz, CDCl$_3$): δ=1.72-1.79 (m, 2H, CH$_2$C$\underline{H}_2$CH$_2$), 1.88 (dt, J=18.3 Hz, 5.7 Hz, 1H, C=CC$\underline{H}$HCH$_2$), 2.12 (dt, J=18.3 Hz, 5.7 Hz, 1H, C=CCH$\underline{H}$CH$_2$), 2.19-2.23 (m, 2H, C(=O)C$\underline{H}_2$CH$_2$), 2.99 (d, J=14.1 Hz, 1H, C(OH)C$\underline{H}$H), 3.05 (d, J=14.1 Hz, 1H, C(OH)CH$\underline{H}$), 3.42 (s, 1H, O$\underline{H}$), 5.82 (s, 1H, C=C$\underline{H}$C=O), 7.36-7.42 (m, 3H, Ar$\underline{H}$), 7.54-7.56 (m, 2H, Ar$\underline{H}$), ppm; $^{13}$C NMR (100 MHz, CDCl$_3$): δ=22.5, 30.9, 37.0, 43.8, 76.8 (q, J$_{C,F}$=28 Hz), 125.3 (q, J$_{C,F}$=285 Hz), 126.1, 128.5, 128.9, 129.6, 130.7, 136.0, 159.0, 199.6 ppm; HRMS (ESI) calcd for C$_{15}$H$_{16}$O$_2$F$_3$ ([M+H]$^+$) 285.1097, found 285.1110.

Compounds 8b to 8j were prepared according to the synthetic method of compound 8a.

3-(3,3,3-Trifluoro-2-hydroxy-2-(p-tolyl)propyl)cyclohex-2-enone (8b)

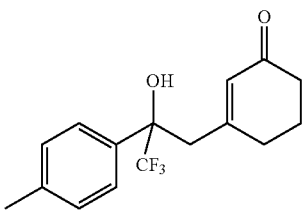

Synthesized by the above procedure, 1.0 h, 119.3 mg (80%).

Colorless solid. $^1$H NMR (400 MHz, CD$_3$OD): δ=1.70-1.77 (m, 2H, CH$_2$C$\underline{H}_2$CH$_2$), 1.99-2.06 (m, 1H, C=CC$\underline{H}$HCH$_2$), 2.14-2.18 (m, 2H, C(=O)C$\underline{H}_2$CH$_2$), 2.21-2.29 (m, 1H, C=CCH$\underline{H}$CH$_2$), 2.33 (s, 3H, ArC$\underline{H}_3$), 2.98 (d, J=14.5 Hz, 1H, C(OH)C$\underline{H}$H), 3.13 (d, J=14.5 Hz, 1H, C(OH)CH$\underline{H}$), 5.78 (s, 1H, C=C$\underline{H}$C=O), 7.18 (d, J=8.0 Hz, 2H, Ar $\underline{H}$) 7.46 (d, J=8.0 Hz, 2H, Ar$\underline{H}$) ppm; $^{13}$C NMR (100 MHz, CD$_3$OD): δ=21.0, 23.6, 32.0, 37.8, 43.9, 77.7 (q, J$_{C,F}$=28 Hz), 127.1 (q, J$_{C,F}$=285 Hz), 127.8, 129.7, 130.7, 135.1, 139.4, 163.4, 202.3 ppm; HRMS (ESI) calcd for C$_{16}$H$_{18}$O$_2$F$_3$ ([M+H]$^+$) 299.1253, found 299.1233.

3-(3,3,3-Trifluoro-2-hydroxy-2-(4-methoxyphenyl)propyl)cyclohex-2-enone (8c)

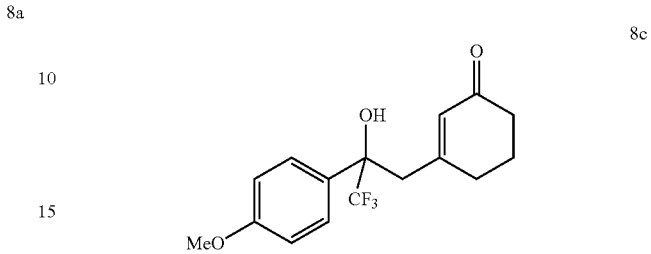

Synthesized by the above procedure, 1.0 h, 131.8 mg (84%).

Colorless solid. $^1$H NMR (400 MHz, CD$_3$OD): δ=1.70-1.77 (m, 2H, CH$_2$C$\underline{H}_2$CH$_2$), 1.99-2.06 (m, 1H, C=CC$\underline{H}$HCH$_2$), 2.14-2.18 (m, 2H, C(=O)C$\underline{H}_2$CH$_2$), 2.21-2.28 (m, 1H, C=CCH$\underline{H}$CH$_2$), 2.97 (d, J=14.4 Hz, 1H, C(OH)C$\underline{H}$H), 3.12 (d, J=14.4 Hz, 1H, C(OH)CH$\underline{H}$), 3.78 (s, 3H, OC$\underline{H}_3$), 5.79 (s, 1H, C=C$\underline{H}$C=O), 6.91 (d, J=8.7 Hz, 2H, Ar $\underline{H}$), 7.50 (d, J=8.7 Hz, 2H, Ar$\underline{H}$) ppm; $^{13}$C NMR (100 MHz, CD$_3$OD): δ=23.6, 32.0, 37.8, 43.9, 55.7, 77.5 (q, J$_{C,F}$=28 Hz), 114.4, 127.1 (q, J$_{C,F}$=285 Hz), 129.1, 129.9, 130.7, 161.1, 163.4, 202.2 ppm; HRMS (ESI) calcd for C$_{16}$H$_{18}$O$_3$F$_3$ ([M+H]$^+$) 315.1203, found 315.1191.

3-(2-(4-Chlorophenyl)-3,3,3-trifluoro-2-hydroxypropyl)cyclohex-2-enone (8d)

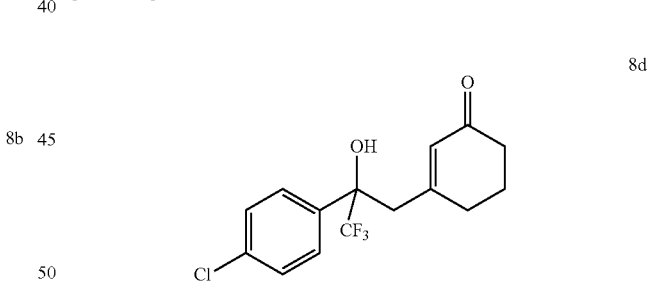

Synthesized by the above procedure, 1.0 h, 105.2 mg (66%).

Colorless solid. $^1$H NMR (400 MHz, CD$_3$OD): δ=1.73-1.80 (m, 2H, CH$_2$C$\underline{H}_2$CH$_2$), 2.01-2.09 (m, 1H, C=CC$\underline{H}$HCH$_2$), 2.15-2.19 (m, 2H, C(=O)C$\underline{H}_2$CH$_2$), 2.23-2.30 (m, 1H, C=CCH$\underline{H}$CH$_2$), 3.01 (d, J=14.1 Hz, 1H, C(OH)C$\underline{H}$H), 3.16 (d, J=14.1 Hz, 1H, C(OH)CH$\underline{H}$), 5.78 (s, 1H, C=C$\underline{H}$C=O), 7.38 (d, J=8.5 Hz, 2H, Ar$\underline{H}$), 7.59 (d, J=8.5 Hz, 2H, Ar$\underline{H}$) ppm; $^{13}$C NMR (100 MHz, CD$_3$OD): δ=23.6, 32.0, 37.8, 43.6, 77.6 (q, J$_{C,F}$=28 Hz), 126.9 (q, J$_{C,F}$=285 Hz), 129.2, 129.7, 130.8, 135.5, 137.0, 162.8, 202.1 ppm; HRMS (ESI) calcd for C$_{15}$H$_{15}$O$_2$F$_3$Cl ([M+H]$^+$) 319.0707, found 319.0693.

3-(2-(4-Bromophenyl)-3,3,3-trifluoro-2-hydroxypropyl)cyclohex-2-enone (8e)

[Chem.73]

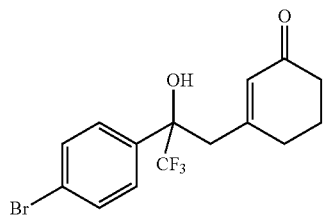

8e

Synthesized by the above procedure, 1.0 h, 127.1 mg (70%).

Colorless solid. $^1$H NMR (400 MHz, CD$_3$OD): δ=1.72-1.79 (m, 2H, CH$_2$CH$_2$CH$_2$), 2.01-2.09 (m, 1H, C=CC HHCH$_2$), 2.15-2.19 (m, 2H, C(=O)CH$_2$CH$_2$), 2.22-2.30 (m, 1H, C=CCHHCH$_2$), 3.00 (d, J=14.6 Hz, 1H, C(OH)C HH), 3.15 (d, J=14.6 Hz, 1H, C(OH)CHH), 5.78 (s, 1H, C=CHC=O), 7.53 (s, 4H, ArH) ppm; $^{13}$C NMR (100 MHz, CD$_3$OD): δ=23.6, 32.0, 37.8, 43.6, 77.6 (q, J$_{C,F}$=278 Hz), 123.6, 126.8 (q, J$_{C,F}$=285 Hz), 129.9, 130.8, 132.3, 137.5, 162.7, 202.1 ppm; HRMS (ESI) calcd for C$_{15}$H$_{15}$O$_2$F$_3$Br ([M+H]$^+$) 363.0202; found 363.0174.

3-(3,3,3-Trifluoro-2-hydroxy-2-(4-(trifluoromethyl)phenyl)propyl)cyclohex-2-enone (8f)

[Chem.74]

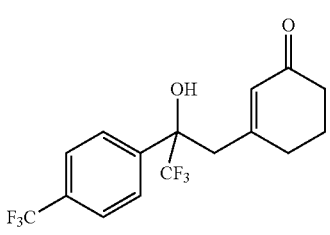

8f

Synthesized by the above procedure, 1.0 h, 107.4 mg (61%).

Colorless solid. $^1$H NMR (400 MHz, CD$_3$OD): δ=1.72-1.79 (m, 2H, CH$_2$CH$_2$CH$_2$), 2.02-2.10 (m, 1H, C=CC HHCH$_2$), 2.13-2.18 (m, 2H, C(=O)CH$_2$CH$_2$), 2.24-2.31 (m, 1H, C=CCHHCH$_2$), 3.06 (d, J=14.8 Hz, 1H, C(OH)C HH), 3.16 (d, J=14.8 Hz, 1H, C(OH)CHH), 5.79 (s, 1H, C=CHC=O), 7.69 (d, J=8.4 Hz, 2H, ArH), 7.82 (d, J=8.4 Hz, 2H, ArH) ppm; $^{13}$C NMR (100 MHz, CD$_3$OD): δ=23.6, 32.0, 37.8, 43.6, 77.6 (q, J$_{C,F}$=28 Hz), 125.5 (q, J$_{C,F}$=270 Hz), 126.0 (q, J$_{C,F}$=4 Hz), 126.8 (q, J$_{C,F}$=285 Hz), 128.8, 130.8, 131.6 (q, J$_{C,F}$=32 Hz 142.6, 162.7, 202.1 ppm; HRMS (ESI) calcd for C$_{16}$H$_{15}$O$_2$F$_6$ ([M+H]$^+$) 353.0971, found 353.0940.

3-(3,3,3-Trifluoro-2-hydroxy-2-(thiophen-2-yl)propyl)cyclohex-2-enone (8g)

[Chem.75]

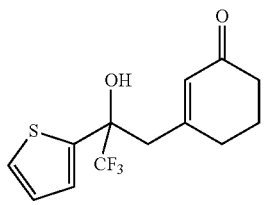

8g

Synthesized by the above procedure, 1.0 h, 110.3 mg (76%).

Colorless solid. $^1$H NMR (400 MHz, CD$_3$OD): δ=1.77-1.83 (m, 2H, CH$_2$CH$_2$CH$_2$), 2.01-2.09 (m, 1H, C=CC HHCH$_2$), 2.19-2.22 (m, 2H, C(=O)CH$_2$CH$_2$), 2.33-2.40 (m, 1H, C=CCHHCH$_2$), 3.00 (s, 2H, C(OH)CH$_2$), 5.81 (s, 1H, C=CHC=O), 7.02 (dd, J=3.6 Hz, 5.1 Hz, 1H, ArH), 7.14 (d, J=3.6 Hz, 1H, ArH), 7.39 (dd, J=1.2 Hz, 5.1 Hz, 1H, ArH) ppm; $^{13}$C NMR (100 MHz, CD$_3$OD): δ=23.7, 32.0, 37.8, 45.3, 77.7 (q, J$_{C,F}$=29 Hz), 126.5 (q, J$_{C,F}$=284 Hz), 126.9 (q, J$_{C,F}$=1 Hz), 127.0, 127.9, 130.8, 142.3, 162.7, 202.2 ppm; HRMS (ESI) calcd for C$_{13}$H$_{14}$O$_2$F$_3$S ([M+H]$^+$) 291.0661, found 291.0650.

3-(3,3,3-Trifluoro-2-hydroxy-2-phenylpropyl)cyclopent-2-enone (8h)

[Chem.76]

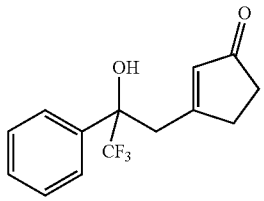

8h

Synthesized by the above procedure, 30 min, 109.4 mg (81%).

Colorless solid. $^1$H NMR (400 MHz, CD$_3$OD): δ=2.18 (t, J=4.6 Hz, 2H, CH$_2$C=O), 2.34-2.42 (m, 1H, C HHCH$_2$C=O), 2.49-2.57 (m, 1H, CHHCH$_2$C=O), 3.21 (d, J=15.7 Hz, 1H, C(OH)CHH), 3.51 (d, J=15.7 Hz, 1H, C(OH)CHH), 5.81 (m, 1H, C=CH C=O), 7.31-7.40 (m, 3H, ArH), 7.62 (d, J=7.5 Hz, 2H, ArH) ppm; $^{13}$C NMR (100 MHz, CD$_3$OD): δ=34.0, 35.9, 39.2, 77.3 (q, J$_{C,F}$=28 Hz), 127.0 (q, J$_{C,F}$=285 Hz), 127.9, 129.2, 129.5, 133.9, 138.0, 179.3, 212.9 ppm; HRMS (ESI) calcd for C$_{14}$H$_{14}$O$_2$F$_3$ ([M+H]$^+$) 271.0940, found 271.0921.

3-(3,3,3-Trifluoro-2-hydroxy-2-(4-methoxyphenyl)propyl)cyclopent-2-enone (8i)

[Chem.77]

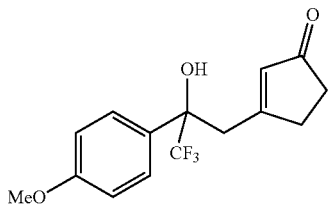

Synthesized by the above procedure, 30 min, 123.2 mg (82%).

Colorless solid. $^1$H NMR (400 MHz, CD$_3$OD): δ=2.19 (t, J=4.4 Hz, 2H, CH$_2$C=O), 2.36-2.42 (m, 1H, CHHCH$_2$C=O), 2.49-2.57 (m, 1H, CHHCH$_2$C=O), 3.18 (d, J=15.6 Hz, 1H, C(OH)CHH), 3.46 (d, J=15.6 Hz, 1H, C(OH)CHH), 3.77 (s, 3H, OCH$_3$), 5.82 (s, 1H, C=C HC=O), 6.91 (d, J=8.8 Hz, 2H, ArH), 7.52 (d, J=8.8 Hz, 2H, ArH) ppm; $^{13}$C NMR (100 MHz, CD$_3$OD): δ=34.0, 35.9, 39.1, 55.7, 77.1 (q, J$_{C,F}$=28 Hz), 114.5, 127.0 (q, J$_{C,F}$=285 Hz), 129.2, 129.7, 133.9, 161.2, 179.6, 213.0 ppm; HRMS (ESI) calcd for C$_{15}$H$_{16}$O$_3$F$_3$ ([M+H]$^+$) 301.1046, found 301.1030.

3-(3,3,3-trifluoro-2-hydroxy-2-(4-(trifluoromethyl)phenyl)propyl)cyclopent-2-enone (8j)

[Chem.78]

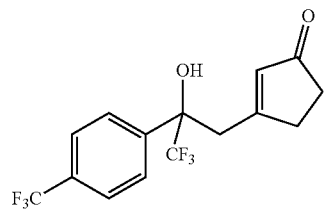

Synthesized by the above procedure, 30 min, 89.5 mg (53%).

Colorless solid. $^1$H NMR (400 MHz, CD$_3$OD): δ=2.21 (t, J=4.7 Hz, 2H, CH$_2$C=O), 2.40-2.46 (m, 1H, CHHCH$_2$C=O), 2.53-2.60 (m, 1H, CHHCH$_2$C=O), 3.25 (d, J=16.0 Hz, 1H, C(OH)CHH), 3.58 (d, J=16.0 Hz, 1H, C(OH)CHH), 5.82 (s, 1H, C=CH C=O), 7.70 (d, J=8.4 Hz, 2H, ArH), 7.85 (d, J=8.4 Hz, 2H, ArH) ppm; $^{13}$C NMR (100 MHz, CD$_3$OD): δ=34.0, 35.9, 38.9, 77.3 (q, J$_{C,F}$=28 Hz), 125.5 (q, J$_{C,F}$=270 Hz) 126.1 (q, J$_{C,F}$=4 Hz), 126.7 (q, J$_{C,F}$=285 Hz), 128.9, 131.8 (q, J=32 Hz), 134.0, 142.5, 178.6, 212.7 ppm; HRMS (ESI) calcd for C$_{15}$H$_{13}$O$_2$F$_6$ ([M+H]$^+$) 339.0814, found 339.0797.

INDUSTRIAL APPLICABILITY

The present invention can provide novel tertiary alcohol derivatives substituted with aryl and trifluoromethyl, and optical isomers thereof which may be used as bioactive substance, enantiomer recognition agent, and synthetic syntons and building blocks. The present invention can also provide the methods for preparation of the tertiary alcohols and their use as enantiomer recognition agent. In addition, the present invention can also provide pharmaceutical composition comprising the tertiary alcohols and their use as therapeutically active substance.

The invention claimed is:

1. A compound of formula I:

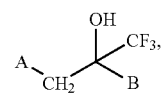

wherein
A is

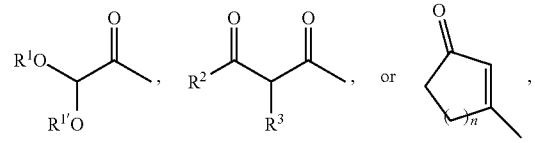

B is aryl which is substituted with one or more groups selected from the group consisting of C$_{1-7}$-alkyl, halogen, halogen-C$_{1-7}$-alkyl, C$_{1-7}$-alkoxy, halogen-C$_{1-7}$-alkoxy, hydroxy, cyano, and nitro, or is heteroaryl, which is unsubstitued or substituted with one or more groups selected from the group consisting of C$_{1-7}$-alkyl, halogen, halogen-C$_{1-7}$-alkyl, C$_{1-7}$-alkoxy, halogen-C$_{1-7}$-alkoxy, hydroxy, cyano, and nitro;

R$^1$ and R$^{1'}$ may be the same or different and each is independently selected from the group consisting of C$_{1-7}$-alkyl, halogen-C$_{1-7}$-alkyl, and C$_{1-7}$-alkyl substituted with one or more C$_{1-7}$-alkoxy; or R$^1$ and R$^{1'}$ may together form C$_{1-7}$-alkylene;

R$^2$ is selected from the group consisting of C$_{1-7}$-alkyl, halogen-C$_{1-7}$-alkyl, C$_{1-7}$-alkoxy, C$_{3-7}$-cycloalkyloxy, halogen-C$_{1-7}$-alkoxy, C$_{1-7}$-alkoxy substituted with one or more C$_{1-7}$-alkyl, and hydroxy;

R$^3$ is selected from the group consisting of hydrogen, halogen, C$_{1-7}$-alkyl, halogen-C$_{1-7}$-alkyl, hydroxy-C$_{1-7}$-alkyl, C$_{1-7}$-alkoxy, and halogen-C$_{1-7}$-alkoxy; and n is 1, 2, 3, or 4;

or a salt thereof.

2. The compound of formula I or salt thereof according to claim 1, wherein

B is aryl which is substituted with one or more groups selected from the group consisting of C$_{1-7}$-alkyl, halogen, halogen-C$_{1-7}$-alkyl, C$_{1-7}$-alkoxy, and halogen-C$_{1-7}$-alkoxy, or is heteroaryl which is unsubstitued or substituted with one or more groups selected from the group consisting of C$_{1-7}$-alkyl, halogen, halogen-C$_{1-7}$-alkyl, C$_{1-7}$-alkoxy, and halogen-C$_{1-7}$-alkoxy.

3. The compound of formula I or salt thereof according to claim 1, wherein

R$^1$ and R$^{1'}$ may be the same or different and each is independently selected from the group consisting of C$_{1-7}$-alkyl, halogen-C$_{1-7}$-alkyl and C$_{1-7}$-alkyl substituted with one or more C$_{1-7}$-alkoxy.

4. The compound of formula I or salt thereof according to claim 1, wherein

37

R² is selected from the group consisting of C₁₋₇-alkyl, halogen-C₁₋₇-alkyl, C₁₋₇-alkoxy, halogen-C₁₋₇-alkoxy, and C₁₋₇-alkoxy substituted with one or more C₁₋₇-alkyl.

5. The compound of formula I or salt thereof according to claim 1, wherein
R³ is selected from the group consisting of hydrogen, halogen and C₁₋₇-alkyl.

6. The compound of formula I or salt thereof according to claim 1, wherein
n is 1 or 2.

7. The compound of formula I according to claim 1, which is selected from the group consisting of
5,5,5-trifluoro-4-hydroxy-1,1-dimethoxy-4-phenylpentan-2-one,
(R)-5,5,5-trifluoro-4-hydroxy-1,1-dimethoxy-4-phenylpentan-2-one,
(S)-5,5,5-trifluoro-4-hydroxy-1,1-dimethoxy-4-phenylpentan-2-one,
4-(4-chlorophenyl)-5,5,5-trifluoro-4-hydroxy-1,1-dimethoxypentan-2-one,
(R)-4-(4-chlorophenyl)-5,5,5-trifluoro-4-hydroxy-1,1-dimethoxypentan-2-one,
(S)-4-(4-chlorophenyl)-5,5,5-trifluoro-4-hydroxy-1,1-dimethoxypentan-2-one,
4-(4-bromophenyl)-5,5,5-trifluoro-4-hydroxy-1,1-dimethoxypentan-2-one,
(R)-4-(4-bromophenyl)-5,5,5-trifluoro-4-hydroxy-1,1-dimethoxypentan-2-one,
(S)-4-(4-bromophenyl)-5,5,5-trifluoro-4-hydroxy-1,1-dimethoxypentan-2-one,
5,5,5-trifluoro-4-hydroxy-1,1-dimethoxy-4-(4-(trifluoromethyl)phenyl)pentan-2-one,
(R)-5,5,5-trifluoro-4-hydroxy-1,1-dimethoxy-4-(4-(trifluoromethyl)phenyl)pentan-2-one,
(S)-5,5,5-trifluoro-4-hydroxy-1,1-dimethoxy-4-(4-(trifluoromethyl)phenyl)pentan-2-one,
5,5,5-trifluoro-4-hydroxy-1,1-dimethoxy-4-(p-tolyl)pentan-2-one,
(R)-5,5,5-trifluoro-4-hydroxy-1,1-dimethoxy-4-(p-tolyl)pentan-2-one,
(S)-5,5,5-trifluoro-4-hydroxy-1,1-dimethoxy-4-(p-tolyl)pentan-2-one,
5,5,5-trifluoro-4-hydroxy-1,1-dimethoxy-4-(4-methoxyphenyl)pentan-2-one,
(R)-5,5,5-trifluoro-4-hydroxy-1,1-dimethoxy-4-(4-methoxyphenyl)pentan-2-one,
(S)-5,5,5-trifluoro-4-hydroxy-1,1-dimethoxy-4-(4-methoxyphenyl)pentan-2-one,
5,5,5-trifluoro-4-hydroxy-1,1-dimethoxy-4-(thiophen-2-yl)pentan-2-one,
(R)-5,5,5-trifluoro-4-hydroxy-1,1-dimethoxy-4-(thiophen-2-yl)pentan-2-one,
(S)-5,5,5-trifluoro-4-hydroxy-1,1-dimethoxy-4-(thiophen-2-yl)pentan-2-one,
5,5,5-trifluoro-4-hydroxy-1,1-dimethoxy-4-(1H-pyrrol-2-yl)pentan-2-one,
(R)-5,5,5-trifluoro-4-hydroxy-1,1-dimethoxy-4-(1H-pyrrol-2-yl)pentan-2-one,
(S)-5,5,5-trifluoro-4-hydroxy-1,1-dimethoxy-4-(1H-pyrrol-2-yl)pentan-2-one,
ethyl 6,6,6-trifluoro-5-hydroxy-3-oxo-5-phenylhexanoate,
(R)-ethyl 6,6,6-trifluoro-5-hydroxy-3-oxo-5-phenylhexanoate,
(S)-ethyl 6,6,6-trifluoro-5-hydroxy-3-oxo-5-phenylhexanoate,

38 ethyl 6,6,6-trifluoro-5-hydroxy-2-methyl-3-oxo-5-phenylhexanoate,
(R)-ethyl 6,6,6-trifluoro-5-hydroxy-2-methyl-3-oxo-5-phenylhexanoate,
(S)-ethyl 6,6,6-trifluoro-5-hydroxy-2-methyl-3-oxo-5-phenylhexanoate,
ethyl 6,6,6-trifluoro-5-hydroxy-5-(4-methoxyphenyl)-3-oxohexanoate,
(R)-ethyl 6,6,6-trifluoro-5-hydroxy-5-(4-methoxyphenyl)-3-oxohexanoate,
(S)-ethyl 6,6,6-trifluoro-5-hydroxy-5-(4-methoxyphenyl)-3-oxohexanoate,
ethyl 5-(4-chlorophenyl)-6,6,6-trifluoro-5-hydroxy-3-oxohexanoate,
(R)-ethyl 5-(4-chlorophenyl)-6,6,6-trifluoro-5-hydroxy-3-oxohexanoate,
(S)-ethyl 5-(4-chlorophenyl)-6,6,6-trifluoro-5-hydroxy-3-oxohexanoate,
ethyl 6,6,6-trifluoro-5-hydroxy-3-oxo-5-(thiophen-2-yl)hexanoate,
(R)-ethyl 6,6,6-trifluoro-5-hydroxy-3-oxo-5-(thiophen-2-yl)hexanoate,
(S)-ethyl 6,6,6-trifluoro-5-hydroxy-3-oxo-5-(thiophen-2-yl)hexanoate,
ethyl 6,6,6-trifluoro-5-hydroxy-5-(4-methoxyphenyl)-2-methyl-3-oxohexanoate,
(R)-ethyl 6,6,6-trifluoro-5-hydroxy-5-(4-methoxyphenyl)-2-methyl-3-oxohexanoate,
(S)-ethyl 6,6,6-trifluoro-5-hydroxy-5-(4-methoxyphenyl)-2-methyl-3-oxohexanoate,
ethyl 5-(4-chlorophenyl)-6,6,6-trifluoro-5-hydroxy-2-methyl-3-oxohexanoate,
(R)-ethyl 5-(4-chlorophenyl)-6,6,6-trifluoro-5-hydroxy-2-methyl-3-oxohexanoate,
(S)-ethyl 5-(4-chlorophenyl)-6,6,6-trifluoro-5-hydroxy-2-methyl-3-oxohexanoate,
ethyl 6,6,6-trifluoro-5-hydroxy-2-methyl-3-oxo-5-(thiophen-2-yl)hexanoate,
(R)-ethyl 6,6,6-trifluoro-5-hydroxy-2-methyl-3-oxo-5-(thiophen-2-yl)hexanoate,
(S)-ethyl 6,6,6-trifluoro-5-hydroxy-2-methyl-3-oxo-5-(thiophen-2-yl)hexanoate,
(R)-ethyl 6,6,6-trifluoro-5-hydroxy-5-phenyl-3-(((R)-1-phenylethyl)amino)hex-2-enoate,
(S)-ethyl 6,6,6-trifluoro-5-hydroxy-3-(((R)-1-phenylethyl)amino)-5-(thiophen-2-yl)hex-2-enoate,
3-(3,3,3-trifluoro-2-hydroxy-2-phenylpropyl)cyclohex-2-enone,
(R)-3-(3,3,3-trifluoro-2-hydroxy-2-phenyl propyl)cyclohex-2-enone,
(S)-3-(3,3,3-trifluoro-2-hydroxy-2-phenyl propyl)cyclohex-2-enone,
3-(3,3,3-trifluoro-2-hydroxy-2-(p-tolyl)propyl)cyclohex-2-enone,
(R)-3-(3,3,3-trifluoro-2-hydroxy-2-(p-tolyl)propyl)cyclohex-2-enone,
(S)-3-(3,3,3-trifluoro-2-hydroxy-2-(p-tolyl)propyl)cyclohex-2-enone,
3-(3,3,3-trifluoro-2-hydroxy-2-(4-methoxyphenyl)propyl)cyclohex-2-enone,
(R)-3-(3,3,3-trifluoro-2-hydroxy-2-(4-methoxyphenyl)propyl)cyclohex-2-enone,
(S)-3-(3,3,3-trifluoro-2-hydroxy-2-(4-methoxyphenyl)propyl)cyclohex-2-enone,
3-(2-(4-chlorophenyl)-3,3,3-trifluoro-2-hydroxypropyl)cyclohex-2-enone, (R)-3-(2-(4-chlorophenyl)-3,3,3-trifluoro-2-hydroxypropyl)cyclohex-2-enone,
(S)-3-(2-(4-chlorophenyl)-3,3,3-trifluoro-2-hydroxypropyl)cyclohex-2-enone,
3-(2-(4-bromophenyl)-3,3,3-trifluoro-2-hydroxypropyl)cyclohex-2-enone,
(R)-3-(2-(4-bromophenyl)-3,3,3-trifluoro-2-hydroxypropyl)cyclohex-2-enone,
(S)-3-(2-(4-bromophenyl)-3,3,3-trifluoro-2-hydroxypropyl)cyclohex-2-enone,
3-(3,3,3-trifluoro-2-hydroxy-2-(4-(trifluoromethyl)phenyl)propyl)cyclohex-2-enone,
(R)-3-(3,3,3-trifluoro-2-hydroxy-2-(4-(trifluoromethyl)phenyl)propyl)cyclohex-2-enone,
(S)-3-(3,3,3-trifluoro-2-hydroxy-2-(4-(trifluoromethyl)phenyl)propyl)cyclohex-2-enone,
3-(3,3,3-trifluoro-2-hydroxy-2-(thiophen-2-yl)propyl)cyclohex-2-enone,
(R)-3-(3,3,3-trifluoro-2-hydroxy-2-(thiophen-2-yl)propyl)cyclohex-2-enone,
(S)-3-(3,3,3-trifluoro-2-hydroxy-2-(thiophen-2-yl)propyl)cyclohex-2-enone,
3-(3,3,3-trifluoro-2-hydroxy-2-phenylpropyl)cyclopent-2-enone,
(R)-3-(3,3,3-trifluoro-2-hydroxy-2-phenylpropyl)cyclopent-2-enone,
(S)-3-(3,3,3-trifluoro-2-hydroxy-2-phenylpropyl)cyclopent-2-enone,
3-(3,3,3-trifluoro-2-hydroxy-2-(4-methoxyphenyl)propyl)cyclopent-2-enone,
(R)-3-(3,3,3-trifluoro-2-hydroxy-2-(4-methoxyphenyl)propyl)cyclopent-2-enone,
3,3,3-trifluoro-2-hydroxy-2-(4-methoxyphenyl)propyl)cyclopent-2-enone,
(S)-3-(3,3,3-trifluoro-2-hydroxy-2-(4-methoxyphenyl)propyl)cyclopent-2-enone,
3-(3,3,3-trifluoro-2-hydroxy-2-(4-(trifluoromethyl)phenyl)propyl)cyclopent-2-enone,
(R)-3-(3,3,3-trifluoro-2-hydroxy-2-(4-(trifluoromethyl)phenyl)propyl)cyclopent-2-enone, and
(S)-3-(3,3,3-trifluoro-2-hydroxy-2-(4-(trifluoromethyl)phenyl)propyl)cyclopent-2-enone,
or a salt thereof.

8. A process for the manufacture of a compound of formula I as defined in claim 1, said process comprising:
a) reacting a compound of formula II:

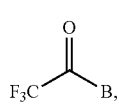

wherein $R^1$ and $R^{1'}$ are defined in claim 1, with a compound of formula III:

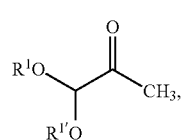

wherein B is as defined in claim 1, in the presence of 1,8-diazabicyclo[5.4.0]undec-7-ene (DBU) to obtain a compound of formula I-1:

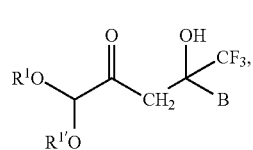

wherein $R^1$, $R^{1'}$, and B are as defined in claim 1, or
b) reacting a compound of formula IV:

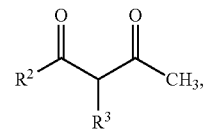

wherein $R^2$ and $R^3$ are as defined in claim 1, with a compound of formula III:

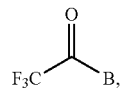

wherein B is as defined in claim 1, in the presence of DBU to obtain a compound of formula I-2:

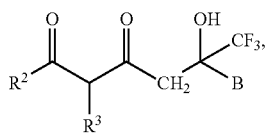

wherein $R^2$, $R^3$, and B are as defined in claim 1, or
c) reacting compound of formula V:

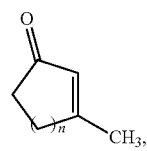

wherein n is as defined in claim 1, with a compound of formula III:

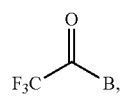

wherein B is as defined in claim 1, in the presence of DBU to obtain a compound of formula I-3:

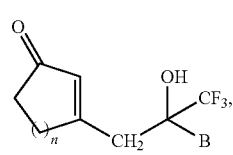

wherein B and n are as defined in claim 1.

9. A process for the manufacture of a compound of formula I-2a:

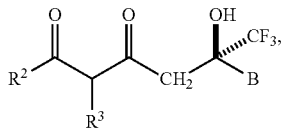
I-2a wherein

B is aryl which is substituted with one or more groups selected from the group consisting of $C_{1-7}$-alkyl, halogen, halogen-$C_{1-7}$-alkyl, $C_{1-7}$-alkoxy, halogen-$C_{1-7}$-alkoxy, hydroxy, cyano, and nitro, or is heteroaryl, which is unsubstitued or substituted with one or more groups selected from the group consisting of $C_{1-7}$-alkyl, halogen, halogen-$C_{1-7}$-alkyl, $C_{1-7}$-alkoxy, halogen-$C_{1-7}$-alkoxy, hydroxy, cyano, and nitro;

$R^2$ is selected from the group consisting of $C_{1-7}$-alkyl, halogen-$C_{1-7}$-alkyl, $C_{1-7}$-alkoxy, $C_{3-7}$-cycloalkyloxy, halogen-$C_{1-7}$-alkoxy, $C_{1-7}$-alkoxy substituted with one or more $C_{1-7}$-alkyl, and hydroxy;

$R^3$ is selected from the group consisting of hydrogen, halogen, $C_{1-7}$-alkyl, halogen-$C_{1-7}$-alkyl, hydroxy-$C_{1-7}$-alkyl, $C_{1-7}$-alkoxy, and halogen-$C_{1-7}$-alkoxy, or a compound of formula I-2b:

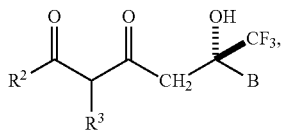
I-2b wherein $R^2$, $R^3$, and B are as defined above, said process comprising d) reacting compound of formula 1-2:

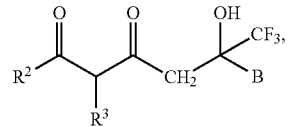
I-2 wherein $R^2$, $R^3$, and B are as defined above, with a chiral amine:

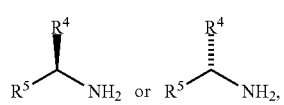

wherein $R^4$ and $R^5$ are independently selected from the group of $C_{1-7}$alkyl and phenyl optionally substituted with halogen, to obtain a compound of formula I-2'-1:

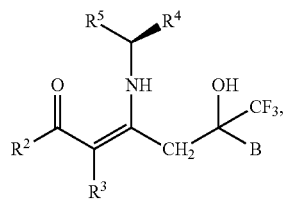
I-2'-1 wherein $R^2$, $R^3$, $R^4$, $R^5$, and B are as defined above, or a compound of formula I-2'-2:

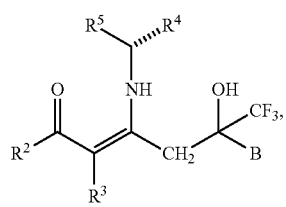
I-2'-2 wherein $R^2$, $R^3$, $R^4$, $R^5$, and B are as defined above.

10. The process according to claim 9, which further comprises e) chiral resolution of the compound of formula I-2'-1:

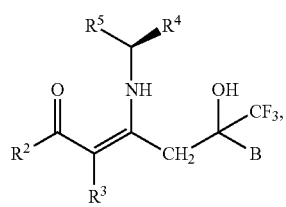
I-2'-1 wherein $R^2$, $R^3$, $R^4$, $R^5$, and B are as defined above, to obtain a compound of formula I-2'-1-1:

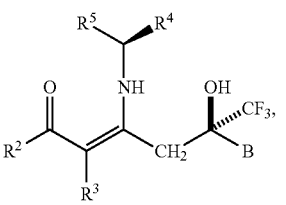
I-2'-1-1 wherein $R^2$, $R^3$, $R^4$, $R^5$, and B are as defined above, or a compound of formula I-2'-1-2:

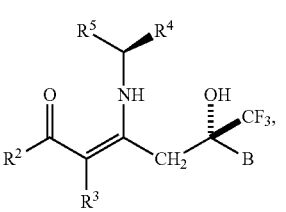
I-2'-1-2 wherein $R^2$, $R^3$, $R^4$, $R^5$, and B are as defined above.

11. The process according to claim 10, which further comprises f) hydrolysis of the compound of formula I-2'-1-1:

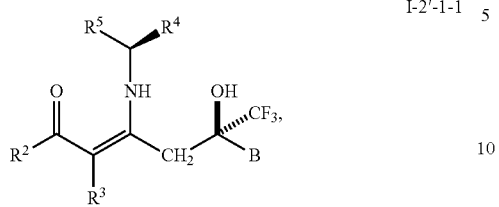

I-2'-1-1 wherein $R^2$, $R^3$, $R^4$, $R^5$, and B are as defined above, or the compound of formula I-2'-1-2:

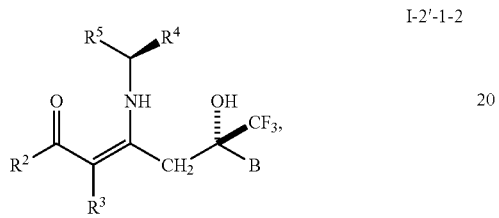

I-2'-1-2 wherein $R^2$, $R^3$, $R^4$, $R^5$, and B are as defined above, to obtain a compound of formula I-2a:

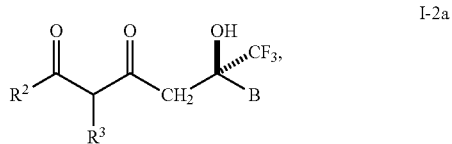

I-2a wherein $R^2$, $R^3$, and B are as defined above, or a compound of formula I-2b:

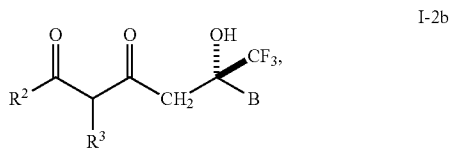

I-2b wherein $R^2$, $R^3$, and B are as defined above.

* * * * *